(12) United States Patent
Mason et al.

(10) Patent No.: US 12,082,597 B2
(45) Date of Patent: Sep. 10, 2024

(54) SUPPLEMENTED FISH FEED

(71) Applicant: CAN TECHNOLOGIES, INC., Wayzata, MN (US)

(72) Inventors: Michael Paul Mason, Balloch (GB); Robin Henderson Strang, Balloch (GB)

(73) Assignee: CAN TECHNOLOGIES, INC., Wayzata, MN (US)

( * ) Notice: Subject to any disclaimer, the term of this patent is extended or adjusted under 35 U.S.C. 154(b) by 0 days.

(21) Appl. No.: 18/050,641

(22) Filed: Oct. 28, 2022

(65) Prior Publication Data

US 2023/0108295 A1    Apr. 6, 2023

Related U.S. Application Data

(60) Continuation of application No. 17/409,492, filed on Aug. 23, 2021, which is a division of application No.
(Continued)

(30) Foreign Application Priority Data

Mar. 15, 2013 (GB) ..................... 1304805
Mar. 14, 2014 (WO) ................ PCT/GB2014/040803

(51) Int. Cl.
*A23K 50/80* (2016.01)
*A23K 20/121* (2016.01)
(Continued)

(52) U.S. Cl.
CPC ............ *A23K 50/80* (2016.05); *A23K 20/121* (2016.05); *A61P 31/04* (2018.01); *A61P 31/10* (2018.01); *A61P 33/00* (2018.01)

(58) Field of Classification Search
CPC ........ A23K 50/80; A23K 20/121; A61P 33/00; A61P 31/04; A61P 31/10
See application file for complete search history.

(56) References Cited

U.S. PATENT DOCUMENTS

| 4,556,562 | A |   | 12/1985 | Larson |           |
|-----------|---|---|---------|--------|-----------|
| 5,695,763 | A | * | 12/1997 | Kleeberg | A01N 65/26 |
|           |   |   |         |        | 424/405   |

(Continued)

FOREIGN PATENT DOCUMENTS

| CN | 102429896 A | 5/2012 |
|----|-------------|--------|
| EP | 0405291 B1  | 8/1994 |

(Continued)

OTHER PUBLICATIONS

Harikrishnan et al., "Supplementation Diet Contatin Probiotics, Herbal and Azadirachtin on Hematological and Biochemical Changes in Cirrhina mrigala Against Aphanomyces invadans". Fisheries and Aquaculture Journal, vol. 2010:FAJ-4. (Year: 2010).*

(Continued)

*Primary Examiner* — Donald R Spamer
*Assistant Examiner* — Assaf Zilbering

(57) ABSTRACT

The present invention relates to feed stuffs for fish to prevent, treat and/or control a variety of diseases, infections and/or infestations in fish. The invention provides supplemented fish feed and other compositions as well as uses and methods exploiting the same. Additionally, the patent provides methods of making supplemented fish feeds.

20 Claims, 26 Drawing Sheets

Related U.S. Application Data

14/776,002, filed as application No. PCT/GB2014/050803 on Mar. 14, 2014, now Pat. No. 11,096,404.

(51) Int. Cl.
  A61P 31/04 (2006.01)
  A61P 31/10 (2006.01)
  A61P 33/00 (2006.01)

(56) References Cited

U.S. PATENT DOCUMENTS

| | | | |
|---|---|---|---|
| 5,856,526 A | 1/1999 | Sankaram | |
| 2010/0254959 A1 | 10/2010 | Lahm | |

FOREIGN PATENT DOCUMENTS

| | | | | |
|---|---|---|---|---|
| JP | 2007131611 A | * | 5/2007 | ............. A61K 36/53 |
| JP | 5364819 B1 | | 12/2013 | |
| WO | 2015021534 A1 | | 2/2015 | |

OTHER PUBLICATIONS

Talpur et al., "Azadirachta indica (neem) leaf dietary effects on the immunity response and disease resistance of Asian seabass, Lates calcarifer challenged with Vibrio harveyi". Fish & Shellfish Immunology 34 (2013) 254-264. (Year: 2013).*
"FAO Specifications and Evaluations for Agricultural Pesticides". Available online at http://www.fao.org/fileadmin/templates/agphome/documents/Pests_Pesticides/Specs/azadirachtin2006.pdf (Year: 2006).*
Blaney et al., "Effect of azadirachtin-derived decalin (perhydronaphthalene) and dihydrofuranacetal (furo [2, 3-fo] pyran) fragments on the feeding behaviour of Spodoptera littoralis." Pesticide science. Feb. 1994;40(2):169-173.
Harikrishnan et al., "Supplementation diet containing probiotics, herbal and azadirachtin on hematological and biochemical changes in Cirrhina mrigala against Aphanomyces invadans." Fisheries and Aquaculture journal 4 (May 24, 2010): 1-11.
Kumar, et al., In vitro and in vivo antiparasitic activity of Azadirachtin against *argulus* spp. in Carassius auratus (Linn. 1758). Parasitol Res, (Nov. 1, 2011), No. 110, pp. 1795-1800.
Salehzadeh et al., "The effects of phytochemical pesticides on the growth of cultured invertebrate and vertebrate cells." Pest Management Science: formerly Pesticide Science. Mar. 2002;58(3):268-276.
Sanderson, "Chemists synthesize a natural-born killer." Nature. Aug. 9, 2007;448(7154):630-632.
Talpur et al., "Azadirachta indica (neem) leaf dietary effects on the immunity response and disease resistance of Asian seabass, Lates calcarifer challenged with Vibrio harveyi." Fish & shellfish immunology 34.1 (2013): 254-264.
Veitch et al., "Synthesis of azadirachtin: a long but successful journey." Angewandte Chemie International Edition. Oct. 8, 2007;46(40):7629-7632.
Mordue and Nisbet. Azadirachtin from the neem tree Azadirachta indica: its action against insects. An. Soc. Entomol. Bras. vol. 29, No. 4 Londrina Dec. 2000.
Certified Translation of JP2007-131611 (Jon et al.), dated May 8, 2020.
Examination Report of AU 2014229794 dated Mar. 9, 2017.
Japan Office Action dated Nov. 14, 2017 re Patent Application No. 2015-562325.
New Zealand Official Action dated Dec. 4, 2019.
Search Report from the Danish Patent and Trademark Office dated Mar. 17, 2015.

* cited by examiner

SUPPLEMENTED FISH FEED

CROSS-REFERENCE TO RELATED APPLICATIONS

This application is a Continuation of U.S. patent application Ser. No. 17/409,492, filed Aug. 23, 2021, which is a Divisional of U.S. Pat. No. 11,096,404, issued Aug. 24, 2021, which is a national phase of International Application No. PCT/GB2014/050803, filed Mar. 14, 2014, which claims the benefit of Great Britain Application No. 1304805.3, filed Mar. 15, 2013, each of which are hereby incorporated by reference in their entirety.

FIELD OF THE INVENTION

The present invention relates to the treatment and/or prevention of pest infections and/or infestations in fish and provides supplemented fish feed and other compositions as well as uses and methods exploiting the same. Additionally, the patent provides methods of making supplemented fish feeds.

BACKGROUND OF THE INVENTION

Pests plague many farmed products and can lead to significant production and economic losses. For example fish, and in particular farmed fish, are susceptible to ectoparasite infections and farmed Atlantic salmon (*Salmo salar*) are prone to sea louse infestations. Left untreated, ectoparasite infections can cause disease and developmental problems in fish.

At present, agents to treat pests may be applied directly to the water (so called bath treatments) or as "in-feed" treatments where the agent is mixed with, or coated on to, the fish feed. For example, organophosphates, hydrogen peroxide and pyrethroids may be exploited in the treatment and/or prevention of ectoparasite infestations in fish. Avermectin compounds may be added to fish feed.

The control of plagues of parasites such as sea lice cost over $450 million a year to the aquaculture industry due to the need to purchase of parasiticides and equipment and to invest staff-time in the management, control and/or research of new parasite control methods Moreover, fish farms are being refused and/or reduced in size due to parasite infestations. There are stress and accidental fish mortalities associated with the treatment of fish with parasiticide treatments, some fish cannot grow to their full size due to fasting before and/or after the treatments and the marketability of fish that have suffered from ectoparasitic infections/infestations may be affected due to their appearance (the parasites can leave marks on the skin of the fish), their reduced size and the consumer's fear to residual antiparasitic agents in the flesh of the fish.

Moreover, the use of (sometimes dangerous) chemicals for parasite control can lead to negative publicity for fish farms due to the associated risk to the staff administering the treatments, the possibility of encountering chemical residues in the fish and the pollution of the environment. Furthermore, the cross-contamination and induction of mass infestations (epizootics) of the parasites between adjacent farms and to wild fish is another major problem associated with these types of infestations. All these factors are leading to increased regulatory control and more expensive farm practices to prevent and control the infestations and the transmission of the parasites.

Bath treatment is the administration of drugs dissolved in water through complete immersion for a pre-determined period. One major advantage of bath treatments, especially when administered using well boats, is that all the parasites are exposed to the same concentration of the drug. Nevertheless, the administration of bath treatments is very labour intensive, the transfer of fish to well boats causes losses of livestock and the agents employed are usually quite toxic and polluting. In-feed treatments are less stressful both for the fish and the farmers and permit simultaneous medication of all fish cages irrespective of the weather conditions, thus reducing the risk of cross-infection associated with the need to apply bath treatments in adjacent cages simultaneously.

However, due to the growing problem of resistance, new ways of treating and/or preventing pest infections and/or infestations are required and it is among the aims of this invention to obviate or mitigate at least one of the problems associated with the prior art.

SUMMARY OF THE INVENTION

In a first aspect, the present invention provides a fish feed comprising a pest control agent.

It should be understood that, where appropriate, the term "comprising" may encompass the terms "consisting essentially of" and "consisting of". For example, the pest control agent comprised within the fish feed of this invention may "consist essentially of" a pest control agent or may "consist of" a pest control agent. Additionally, each of the definitions provided in this specification applies to each aspect of this invention.

A fish feed may comprise any substrate which is edible to fish. The substrate may or may not provide a source of nutrition and therefore this invention encompasses feeds which are either nutritional feeds or feeds which are not intended to be nutritional (i.e. are non-nutritional). A fish feed may be any feed suitable for feeding to fish. Nutritional fish feeds may comprise a food stuff formulated for fish as part of its diet and a fish feed of this invention may comprise one or more ingredients to provide fish with a source of nutrition. By way of example, the fish feed may comprise fish meal which may itself comprise one or more nutritional components. The fish meal component of a fish feed for use in this invention may comprise plant and/or animal derived matter. Any animal derived matter may be derived from a fish and/or some other (heterologous or non-fish) species. Suitable fish feeds may comprise proteinaceous material (as a source of proteins, peptides and/or amino acids), carbohydrates and fats. Additionally or alternatively, a fish feed may comprise one or more compounds designed to alter the quality, quantity and/or appearance of a fish tissue. For example, a fish feed may comprise a carotenoid compound to improve the appearance (colour) of the muscle tissue in a fish.

As such, this invention provides nutritional and/or non-nutritional fish feeds comprising a pest controlling agent. The non-nutritional fish feeds may comprise some form of substrate which is edible by fish.

The fish feed of this invention may be provided in liquid or solid form. Solid form feeds may comprise pellets and/or flakes.

One of skill will be familiar with suitable types of fish feed and would appreciate that for any given fish species, the most appropriate feed formulation and/or form (for example solid feed and/or liquid feed), may vary.

The fish feed provided by this invention may be used to feed wild and/or farmed fish. In this regard, the fish feed may be used to feed fresh water and/or salt water (marine) fish.

The feeds provided by this invention may be fed to or used to feed any fish which is susceptible to infection/infestation by one or more pests. For example, the feed may find particular application in aquaculture as a component of a diet fed to any farmed fish including, for example, commercially relevant fish species. For example, the feeds provided by this invention may form part of diet fed to fresh, brackish and/or sea water fish. For example, the feed of this invention may find application as a component of a diet fed to species belonging to the families Cyprinidae, Cichlidae, Pangasiidae, Sciaenidae, Serranidae, Carangidae, Sparidae, lateolabracidae, Moronidae, Mugilidae, Cypriniformes, Latidae, Eleotridae, Tilapiini and Salmonidae. As such, the fish feed of this invention may be used to feed species belonging to any of the genera within these families and in particular, those species which are farmed for human or animal consumption. For example (and without being limited to any particular examples) the fish feed described herein may be used to feed species belonging to the genera *Salmo* and/or *Oncorhynchus*. In particular, the fish feed may be used to feed wild and/or farmed salmon and/or trout species including, for example, Atlantic Salmon (*Salmo salar*), Pacific salmon and/or Rainbow trout. Moreover, the fish feed may be used as a fish pest control agent for other fish species within the aquaculture industry such as Sea Bass or Bream, as well as in the pet/decorative fish industry, for example for pest control in goldfish (*Carassius auratus*).

As such, this invention provides a fish feed for species within the family Salmonidae, wherein said feed comprises a pest controlling agent.

The term "pest" may, for example, encompass any organism which is detrimental to the health, value and/or appearance of another organism. The term pest may include species of ecto/endo-parasites (for example worms, helminths, flukes, lice, mites and/or ticks), bacteria, viruses, fungi and/or protozoa (including, for example amoeba).

As such, a fish feed of this invention may comprise an agent for controlling an infection/infestation caused or contributed to by a parasite, bacteria, virus, fungus and/or protozoa. Each agent comprised within the fish feed of this invention may be individually capable of controlling one or more of a parasitic, bacterial, viral, fungal or protozoal infections/infestations.

One of skill will appreciate that where the pest is a parasite, the parasite may be an endoparasite or an ectoparasite. As such, the fish feed of this invention may comprise agents for controlling endoparasite and/or ectoparasite infections/infestations.

The term "endoparasites" may encompass organisms which inhabit one or more internal niches of another organism. For example, an endoparasite may inhabit one or more of the tissues, organs or systems of a host organism. For example an endoparasite may inhabit the gut and/or blood of a host organism. The term "ectoparasite" may include organisms which inhabit or occupy an external niche of another species. For example, an ectoparasite may inhabit or occupy the surface of a host species. In the case of fish, ectoparasites may inhabit the skin of the fish (sometimes lodging between scales) feeding off the mucus, blood skin and/or gills.

Ectoparasites of fish may comprise species belonging to the phylum Arthropoda. As such, the term "ectoparasites" includes crustaceans and species of lice which inhabit fish hosts. By way of example, in the case of fish belonging to the family Salmonidae (for example *Salmo* and/or *Oncorhynchus* spp.), the pest control agent of the fish feed provided by this invention may control, for example, lice infections and/or infestations. The pest control agent of the fish feed provided by this invention may control ectoparasites such as *Argulus* ssp or *Caligus* ssp. In particular, the pest control agent for use in the fish feed described herein may be effective at controlling copepod infections/infestations of fish.

A species of copepod which is an ectoparasite of the Atlantic salmon belongs to the *Lepeophtheirus* genus and is known as the salmon louse (*Lepeophtheirus salmonis*). Other types of copepod ectoparasite of fish belonging to the family Salmonidae are *Caligus clemensi* and *Caligus rogercreseyi*. Lice, including, for example, Salmon lice, are ectoparasites which feed off the blood, mucus and skin of Salmon species. The life cycle of the salmon louse comprises a number of stages beginning with the free swimming nauplius stages. After these stages, the nauplius develops into the copepodit stage which attaches itself to the fish. From this point the copepodit develops through the chalimus stages and grows to a length of about 5 mm (male) and about 10 mm (female). The chalimus then progresses to the pre-adult and adult stages. In the pre-adult and adult stages the louse is mobile and can move around the host and from one host to another.

As such, this invention provides a fish feed comprising an agent capable of treating, preventing and/or controlling *Lepeophtheirus* infections and/or infestations. The *Lepeophtheirus* infection and/or infestation may be caused and/or contributed to by the salmon louse, *Lepeophtheirus salmonis*. In this case, the fish feed may be for species belonging to the family Salmonidae. For example the fish feed may be a *Salmo* and/or *Oncorhynchus* spp. feed. However, one of skill will appreciate that the feed may be given to any fish which is susceptible to a *Lepeophtheirus* infection and/or infestation.

An agent which "controls" a pest (referred to herein as a pest "controlling agent") may be any agent which affects, facilitates or contributes to the eradication or reduction of a pest infection/infestation of a fish. Additionally, or alternatively, suitable agents may cure, ameliorate or improve one or more of the symptoms associated with a pest infection/infestation. Pest controlling agents for use in this invention may be biologically active to one or more fish pests and suitable agents may kill or repel pests. Agents may additionally, or alternatively, modulate (for example inhibit or adversely affect) the behaviour (for example feeding habits/patterns) and/or life cycle of a pest. Agents affecting the life cycle of a pest may affect its general development (modulating growth and/or development through one or more phases of the life cycle) and/or fecundity (general fertility and/or egg production).

In general, agents for use in this invention may be referred to as having anti-parasite, anti-bacterial, anti-viral, anti-fungal and/or anti-protozoal effects. An anti-parasite agent for use in this invention may be used to control endoparasites and/or ectoparasites. Agents of this type may be referred to as having anti-ectoparasite and/or anti-endoparasite effects. It should be understood that any given agent for use in any aspect of this invention may exhibit one or more of an anti-parasite (anti-ectoparasite, anti-endoparasite), anti-bacterial, anti-viral, anti-fungal and/or anti-protozoal effect.

This invention may provide a fish feed comprising an anti-ectoparasite agent, wherein said agent exhibits one or more properties selected from the group consisting of:

(i) toxicity to ectoparasites;

(ii) modulation of ectoparasite behaviour; and
(iii) modulation of at least one component and/or phase of the life cycle of an ectoparasite, including, for example, egg development, egg deposition, viability of eggs and/or feeding behaviour.

The pest control agents of this invention may facilitate the treatment and/or prevention of a pest infection/infestation. Accordingly, the fish feed provided by this invention may be suitable for use (perhaps as a form of medicament) for treating and/or preventing pest infections/infestations of fish. A medicament for use in treating a pest infestation and/or infection of fish (for example an ectoparasite infection/infestation) may comprise a substrate edible by fish and a pest controlling agent.

It should be understood that the fish feed of this invention may comprise, or be supplemented with, one or more pest controlling agents. Where a fish feed comprises, or is supplemented with, at least two or more different pest controlling agents, each pest controlling agent may be individually active (or biologically active) to and/or capable of modulating the behaviour and/or development of, a pest. Each agent may be individually effective against one or more different pests.

Without wishing to be bound by theory, it is suggested that any pest controlling agent provided as a component of a fish feed may adversely affect pests that feed off their hosts and, for example, take blood, or mucus meals therefrom. Upon exposure to the agent, the pest may be modulated (i.e. the development/behaviour of the pest may be modulated), killed and/or repelled from the host.

Pest controlling agents suitable for use in this invention may comprise one or more synthetic and/or natural agents.

A pest control agent for use in this invention (i.e. the "active ingredient") may comprise a compound or compounds obtainable from a plant belonging to the genus *Azadirachta*. For example, the agent may comprise an extract of a plant belonging to the genus *Azadirachta*. The agent may be obtainable or extracted from *Azadirachta indica* —a tree commonly known as the "Neem" tree. The agent may be obtainable or extracted from any part of the plant including, for example the leaves, stems, bark, fruit and/or seeds thereof.

Extracts (compositions and agents for example) obtained or obtainable from the Neem tree may comprise a range of complex terpenoid compounds (tetranortripenoids or limonoids). The most potent of the many terpenoids are a group of compounds called the azadirachtinoids.

The pest control agent for use in this invention may comprise one or more azadirachtinoids.

The (pest control) agent for use in this invention may comprise the tetranortriterpenoid compound, azadirachtin. "Azadirachtin" is the collective term applied to a large group of insecticidally-active limonoids. One of the azadirachtins (namely azadirachtin A) may otherwise be known as dimethyl [2aR-[2aα,3β,4β(1aR*,2S*,3aS*,6aS*,7S*,7aS*), 4aβ,5α,7aS*,8β(E),10β,10aα,10bβ]]-10-(acetyloxy)octahydro- 3,5-dihydroxy-4-methyl-8-[(2-methyl-1-oxo-2-butenyl)oxy]-4-(3a,6a,7,7a)-tetrahydro-6a-hydroxy-7a-methyl-2,7-methanofuro[2,3-b]oxireno[e]oxepin-1a(2H)-yl)-1H,7H-naphtho-[1,8-bc:4,4a-c']difuran-5,10a(8H)-dicarboxylate.

Azadirachtin A (Azadirachtin A) is the most abundant of a group of the azadirachtinoid congeners. Azadirachtin A makes up about 80% of the azadirachtinoids in the neem seed kernels. The structural formula of azadirachtin A is:

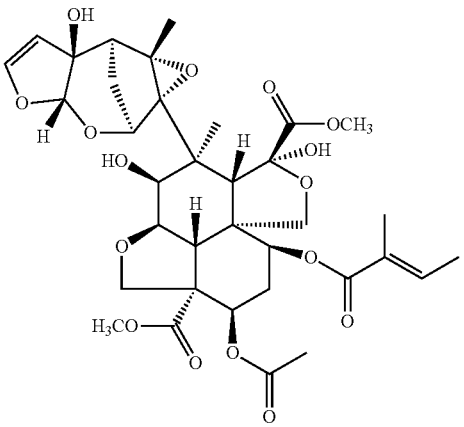

It should be noted that the term "azadirachtin" as used herein is intended to encompass not only all naturally occurring variants or derivatives of azadirachtin (for example, including but not limited to azadirachtins A, B, D, E, F, G, H, I, K) but also all synthetic variants, fragments, analogues and/or derivatives. In this regard, one of skill will appreciate that any azadirachtin variants, fragments, derivatives and/or analogues for use in this invention should be functional, that is to say they exhibit at least one anti-pest property.

Azadirachtin may be synthetically produced using, for example, the method of Veitch et al, 2007 (Synthesis of azadirachtin: a long but successful journey: *Agnew. Chem. Int. Ed. Engl.* 46(40): 7629-32: see also Sanderson, 2007: Chemists synthesize a natural born killer": Nature 448 (7154): 630-1). Suitable azadirachtin fragments (i.e. fragments which are functional) may be found in "The effects of phytochemical pesticides on the growth of cultured invertebrate and vertebrate cells"; Salezadeh A., Jabbar, A., Jennens, L, Ley, S. V. Annadurai, R, Adams, R., Strang, R. H. C. Pest Manag. Sci 58, 268-276, (2002) and "Effect of azadirachtin-derived decalin (perhydronaphthalene) and dihydrofuranacetal (furo(2,3-b)pyran) fragments on the feeding behaviour of *S. littoralis*"; Pest. Sci. 40, 169-173 (1994). The contents of all of these documents are incorporated herein by reference in their entirety.

It may also be possible to produce azadirachtin using recombinant technology and/or cell culture techniques. For example, cells derived from plants belonging to the genus *Azadirachta* may be cultured under conditions in which they express azadirachtins.

Alternatively, azadirachtin may be extracted from *Azadirachta indica* (for example from one or more of the leaves, stems, bark, fruit and/or seeds) by one or more extraction processes. Suitable methods of extraction will be known to those skilled in the field and may include, for example, techniques which exploit mechanical pressing of neem seeds (kernels) and the use of non-polar solvents. Additionally or alternatively, solvent extraction techniques exploiting, for example, alcohol and those described in U.S. Pat. Nos. 4,556,562 and 5,695,763 (derived from WO9216109 and including EP0579624) (the contents of all of these documents is incorporated herein by reference in their entirely) may be exploited as a means to produce "azadirachtin-rich" pest control agents for use in the fish feed of this invention. For example, azadirachtin may be effectively recovered from the seeds of the neem tree by crushing the seeds, extracting azadirachtin from the crushed seeds with water and then either extracting azadirachtin from the water using a non-aqueous solvent which is not miscible with water and has a higher solubility of azadirachtin than water or a surfactant having a turbidity temperature between 20° C. and 80° C. The concentrated azadirachtin is easily recovered from the second extraction solution and shows high activity as an insecticide. Extraction methods employing polar solvents (e.g. water) lead to extracts that are rich in polar components.

For the avoidance of doubt, it should be clear that compositions described as (or comprising) neem oil and/or margosa extract may be very different from the pest control agents of this invention. The pest control agent of the present invention is richer in the azadirachtinoid active ingredients (in particular azadirachtin A) than neem oil and other oil-based formulations. This is due to the fact that azadirachtinoids such as azadirachtin A are relatively polar complex terpenoids with a large number of oxygen functionalities, which make the molecules moderately water-soluble (2 g.L$^{-1}$). As a result, azadirachtinoids (especially azadirachtin A) are present in much higher concentration in the extracts obtained employing polar solvents than in neem oil and/or margosa extracts. Without wishing to be bound by theory, the bioavailability of the active ingredients to the target parasite in the water-based extract may be greater than in the neem oil, given the increased solubility and/or miscibility of the water-based extract in/with water.

Thus, the pest control agent of the present invention may not be, comprise, consist or consist essentially of, neem oil. The pest control agent (active ingredient) of the fish feed provided by this invention may comprise, consist or consist essentially of azadirachtin A.

The active ingredient and/or agent may comprise NeemAzal® and/or NeemAzal® Technical. It should be understood hereinafter that the term "NeemAzal®" refers to any formulations comprising NeemAzal®, including NeemAzal® Technical.

NeemAzal® is sold for primary use in plant insect control. The use of NeemAzal® in plants has been shown to lead to feeding inhibition in insect pests. NeemAzal® has also been shown to inhibit insect moulting, reduce fecundity and breeding ability. NeemAzal® may be prepared from neem kernels using the aqueous extraction process of U.S. Pat. No. 5,695,763. The NeemAzal® (plant protection) formulation may comprise a naturally based neem extract, plant oil and a surfactant.

NeemAzal® Technical is an extract of neem seeds made with polar solvents, greatly enriched in azadirachtin A. It is a much more stable extract than, for example, neem oil or other neem oil-based extracts. NeemAzal® Technical may contain 35±2% (35 000 ppm) azadirachtin A. Other minor azadirachtinoids make up a further 32% of the weight. The remainder may be composed of small amounts of other terpenoids (salannin (3-5%) and nimbin (3-5%)), without biological activity, along with some protein and polysaccharide.

The composition of NeemAzal® Technical may comprise (% w/w):

Azadirachtin A 34
Azadirachtin B approx. 5.5
Azadirachtin D approx. 2.1
Azadirachtin E≤1
Azadirachtin F≤1
Azadirachtin G≤1
Azadirachtin H approx. 2.3
Azadirachtin I approx. 0.8
Azadirachtin K and other Azadirachtins<2
Azadirachtinin approx. 2
Sum of Azadirachtins: 51.7%

NeemAzal® formulations for use in this invention may comprise dilutions of NeemAzal® Technical.

A suitable pest control agent for use in this invention may be sold under the name Riddance®. Riddance® comprises azadirachtin.

In view of the above, the present invention provides a fish feed comprising azadirachtin and/or azadirachtin A. The fish feed may be a nutritional feed or anon-nutritional feed comprising a substrate edible by fish.

The present invention further provides a fish feed comprising NeemAzal® Technical. The fish feed may be a nutritional feed or a non-nutritional feed comprising a substrate edible by fish.

The invention may further provide a fish feed, for example a feed suitable for feeding to species within the family Salmonidae, said feed comprising a pest controlling agent, wherein the pest control agent comprises one or more agents selected from the group consisting of:
  (i) azadirachtin (naturally sourced (i.e., extracted from *Azadirachta indica*) and/or synthetically produced (perhaps using cell culture techniques));
  (ii) azadirachtin A (naturally sourced (i.e., extracted from *Azadirachta indica*) and/or synthetically produced (perhaps using cell culture techniques));
  (iii) a neem extract enriched in azadirachtin A;
  (iv) NeemAzal® Technical;
  (v) NeemAzal® formulations;
  (vi) synthetic azadirachtin produced by the method of Veitch et al, 2007;
  (vii) a functional azadirachtin, variant, derivative and/or analogue thereof; and
  (viii) an azadirachtin A-rich formulation obtainable by the method described in U.S. Pat. Nos. 4,556,562 and/or 5,695,763.
  (ix) Riddance®

It should be understood that agents prepared from plant extracts may be complex in nature and may comprise additional components not described herein. In the case of extracts prepared from plants belonging to the genus *Azadirachta* (for example *Azadirachta indica*), the extract may not only comprise azadirachtin (for example azadirachtin A and/or other azadirachtin variants), but many other components including quantities (sometimes minute quantities) of, for example, the limonoids Salannin, Nimbin and 6-desacetylnimbin.

For the avoidance of doubt, the fish feed provided by this invention may comprise one or more of the pest control agents described herein together with one or more other agents. For example, the fish feed may comprise azadirachtin A, NeemAzal®, NeemAzal® Technical and/or any of the pest control agents defined herein together with one or more other agents. The one or more or other agents may comprise anti-ectoparasite agents (including the any of the pest control agents (e.g. azadirachtin A and/or NeemAzal® Technical) described herein), antimicrobial agents (antibiotic, anti-bacterial, anti-fungal, anti-viral agents), anti-parasitic agents (for example anti-endoparasite agents), anti-protozoal agents and/or nutritional supplements and the like. The one or more other agents may or may not be mixed with or coated on (or layered within) the fish feed. The one or more other agents may be provided separately (either in liquid or solid form) and administered separately (before or after) or concurrently with a feed of this invention. The pest controlling agent may be incorporated into or mixed with the fish feed. The agent may be mixed with the feed during its manufacture such that it becomes distributed through all or a part of the fish feed. Once the agent has been mixed with the fish feed, the fish feed/agent mixture may be formed into, for example, pellets and/or flakes as required.

The agent may be applied to the fish feed as one or more layers or coats. For example, the agent may be applied to an outside surface of a pellet or a flake—in this way a fish feed pellet or flake may become wholly or partially coated with the agent. One or more layers or coats of agent may be applied to an outside surface of a fish feed flake or pellets. Any layer or coating of agent, may be "sealed" or protected by the application of one or more additional coats or layers of a sealing substance. By way of example, a layer or coat of agent may be sealed by the application of a layer or coat of fish oil. Additionally, or alternatively, one or more further layers or coats of fish feed may be applied to the (optionally sealed) coat or layer of fish feed. In this way, any given fish feed flake or pellet may comprise multiple layers of fish feed, sealing substance and/or agent.

While any of the agents described herein may be mixed with, coated on or layered within the feeds of this invention, the pest control agent may additionally or alternatively, be provided separately for administration before/after or concurrently with, a fish feed (including a feed of this invention). The fish feed may lack a pest control agent—the pest control agent being provided as a composition to be administered separately as described.

As such, this invention further provides a composition for administration to fish, the composition comprising a pest control agent as defined herein. For example, the composition may comprise azadirachtin, extracts enriched in azadirachtin A, NeemAzal® formulations, NeemAzal® Technical and/or any of the pest control agents described herein. The composition may comprise a liquid or solid excipient, diluent and/or carrier. The composition may be formulated for adding to water so as to permit a "bath-treatment" type administration of the composition to fish. Alternatively, the composition may be provided in a form which is edible by fish. The composition may also be formulated for parenteral administration. Thus, the composition may comprise pharmaceutically acceptable carriers, diluents and/or excipients. Furthermore, the composition may be sterile.

A composition of the invention may be administered before during or after the administration of any of the fish feeds described herein. Compositions of the invention may be liquid and/or solid compositions comprising one or more of the pest control agents described herein such as, for example, azadirachtin, azadirachtin A, NeemAzal® and/or NeemAzal® Technical.

Treatments which exploit supplemented fish feeds of the type described herein may be referred to as "in feed treatments". Thus this invention provides "in-feed" treatments for the treatment, control and/or prevention of fish pests—in particular ectoparasites. However, fish which are sick and/or infested/infected with parasites and/or less aggressive fish may eat less and may consume lower doses of the treatment (Ibgoeli et al., 2014).

Thus, treatments regimes which are based on the use of both supplemented feeds and compositions of this invention may be particularly useful for treating fish whose appetite is affected by illness, infection and/or infestation and/or less aggressive fish that eat less. In such cases (and without wishing to be bound by theory) a composition of the invention (comprising azadirachtin) may be applied to the water as a bath treatment—this may begin to affect the treatment and in those fish whose appetite has been adversely affected by illness, infection and/or infestation, the fish may begin to regain an appetite as the parasite burden lessens. The fish may then be fed a fish feed of this invention (supplemented with azadirachtin). The feed may be administered concurrently with and/or separately from, the composition. "In-feed" type treatments may be preferable to bath-type treatments and therefore, the use compositions of this invention to promote an initial treatment which improves a fish's appetite may facilitate the ultimate use of an "in-feed" treatment. Moreover, in less aggressive (or low feeding fish) the concurrent use of a composition of this invention may boost or ensure the correct azadirachtin dose is administered to a fish.

Generally, the dose/amount of pest controlling agents added to a feed or composition of this invention will be set so as to achieve the desired pest control effect. One of skill will appreciate that the exact amount of pest control agent to be added to a fish feed (or composition) of this invention, may vary depending on, for example, the species of fish and/or the number of fish to be fed. Other factors that influence the amount of agent added to the feed include, for example, the presence of possible competitors for the feed (i.e. other non-target animal species that may eat the fish feed), the type of pest to be controlled, the age/maturity of fish, the season, the water type (pH, salinity, purity, temperature), the temperature and aggressiveness of the fish.

Where the agent is (or comprises) for example azadirachtin (A) and/or NeemAzal® Technical, the fish feed of this invention may be formulated such that the dose of agent administered to the fish through the feed may be approximately 1-100 mg, 1-90 mg, 1-80 mg, 1-70 mg, 1-60 mg, 5-50 mg NeemAzal® Technical per kg body weight/day, about 10-40 mg NeemAzal® Technical per kg body weight/day, about 15-35 mg NeemAzal® Technical per kg body weight/day, about 20-30 mg NeemAzal® Technical per kg body weight/day or about 25 mg NeemAzal® Technical per kg body weight/day.

A composition and/or feed of the present invention may be administered for as long as required to achieve the desired pest control effect. For example, the composition and/or feed may be administered over about a 1-10 day period, about 2-8 days, about 3-7 days, about 4-6 days, about 5 days. Typically, the feed may be administered for about 7 days. Alternatively, the composition and/or fish feed of the invention may be administered at a low dose for a longer period of time. It should be understood that the administration regime of the composition and/or feed of the invention may be of a variable length in order to adjust to different doses.

During the period of administration, the composition and/or feed may be administered as many times as required to achieve the desired pest control effect. For example, the composition and/or feed of the present invention may be administered about 1, 2, 3, 4 or more times a day.

The fish feed of this invention may be at least partially coated with agent.

About 0.1 -100 g, about 90 g, about 80 g, about 70 g, about 60 g, about 50 g, about 40 g, about 30 g, about 20 g, about 1-10 g, about 2-9 g, about 3-7 g, about 4-6 g or about 5 g NeemAzal® Technical may be used per kilogram of feed. One of skill will appreciate that this equates to about 0.01-10% w/w (NeemAzal® Technical/feed).

Surprisingly, the inventors have discovered that pest controlling agents which comprise, consist essentially of, or consist of azadirachtin A, NeemAzal® Technical and/or any of the neem extract agents described herein, exhibit not only anti-ectoparasite effects in fish, but also anti-fungal and anti-protozoal effects too. Moreover, despite the relative instability of anti-ectoparasite agents which comprise azadirachtin A and/or NeemAzal® Technical in water, when applied to a fish feed, azadirachtin A, NeemAzal® Technical and/or any of the neem extract-containing agent and/or agents are rendered at least temporarily stable such that the active ingredients of the composition and/or fish feed (namely the anti-ectoparasite agents) may exhibit their full biological activity over a pro-longed period of time. Without wishing to be bound by theory, the half-life of NeemAzal® Technical in water is 8 days, however when NeemAzal® Technical is contained in a fish feed of the invention, there is no sign of deterioration in water after about 48 h.

As such, the present invention provides compositions and/or fish feeds comprising the azadirachtin-based agents described herein for use as a fish pest control agent, wherein the agent is rendered at least temporarily stable so that the active ingredients of the composition exhibit their full biological activity.

In addition, it should be noted that azadirachtin A, NeemAzal® Technical and/or any of the neem extract agents of the invention exhibit no toxic effects on fish or humans and are therefore safe to use in both wild and farmed fish stocks.

The azadirachtinoids, of which azadirachtin A is the predominant example, have a number of characteristics of significance:
a) They are highly specific in their targets; arthropods and other invertebrates are generally sensitive, but the extracts are almost totally innocuous to higher animals. Indeed NeemAzal® Technical is used as part of IPM in horticulture together with wasps and ladybirds.
b) They are not neurotoxins but appear to have several molecular targets. They have no immediate knock-down effect but have their effect over periods of days to weeks.
c) They have a short half-life in the environment.
d) Although they have been used as commercial biocides and plant protection products for almost 20 years in the USA and EU, as yet there have been no reports of signs of resistance in target organisms.

One dominant fact arising from the huge amount of work done with insects and mites in the assessment of azadirachtin-containing extracts is that while arthropods and other invertebrates are sensitive to the active ingredient (i.e. azadirachtin A), higher organisms, including mammals, are unaffected. The dose for acute lethality for NeemAzal® Technical in rats is >5000 mg.kg$^{-1}$ body weight. Chronic adverse effects are absent, and there is no sign of carcinogenic effect or on reproduction. The Pesticide Manual places azadirachtin A in the least toxic category (V).

Furthermore, since azadirachtin A, NeemAzal® Technical and/or any neem extract of the invention are readily soluble in water, they do not reside and accumulate in fish. Rather, once administration has ceased, the agent may quickly lose effectiveness, as it is metabolised, degraded and/or excreted. In the case of farmed fish stocks, this ensures a reduced time to harvest following administration of a fish feed or composition of this invention.

Often, waste or non-consumed fish feed is a concern as it can pollute the environment. This is particularly true of fish feeds that have been supplemented with one or more therapeutic compounds which, if not consumed, can accumulate in the environment causing damage to ecosystems and other organisms. The compositions comprising azadirachtin A, NeemAzal® Technical and/or any of the neem extract agents described herein rapidly breakdown in the environment, reducing the risk of contamination.

In common with most plant-derived biocides, the azadirachtin terpenoids have a short half-life in the environment. They hydrolyse in water, and their disappearance is faster the more alkaline the water. For example, at pH 7.0 and 20° C. the half-life of azadirachtin terpenoids is 19.5 days, and at pH 8.0 it is 4.4 days. As seawater is slightly alkaline, (pH 7.5-8.4) any dissolved azadirachtin terpenoids will have largely disappeared within a week. Azadirachtin is rapidly catabolized by the microflora in soil. The half-life in various soils has been found to average 3 days. Preliminary studies with some sediment from below cages in Skye (Scotland) and subsequently infused with NeemAzal® in the laboratory have indicated a half-life of 3 weeks for NeemAzal® Technical added to the sediment and incubated at 15° C. Unchanged excreted material will be infinitely diluted in the water and hydrolyzed within days into small fragments without biological activity.

Therefore, the present invention provides a composition and/or fish feed comprising azadirachtin for use as a fish pest control agent, wherein the compositions comprising azadirachtin A, NeemAzal® Technical and/or any of the pest control agents described herein rapidly break down in the environment, reducing the risk of contamination.

In addition, the inventors have discovered that while anti-ectoparasite agents comprising azadirachtin A, NeemAzal® Technical and/or any of the neem extract agents described herein are known to exhibit potent insecticidal properties, when administered to fish and/or present as a supplement of fish feed, pest control agents of this type exhibit a potent anti-ectoparasite effect. Indeed, the inventors have shown that NeemAzal® Technical may have a substantial effect upon *Lepeophtheirus salmonis* in Atlantic salmon. Fish feed supplemented with NeemAzal® Technical (coated thereon or incorporated therein) may bring about a reduction in (i) the numbers of *Lepeophtheirus salmonis* chalimus attached to Atlantic salmon, (ii) the number of pre-adults developing to adults, (iii) egg production in females, (iv) the total number of adult females and (v) the proportion of gravids. In particular, the inventors have noted that in fish (*Salmo salar*) infected with *Lepeophtheirus salmonis* chalimus and pre-adult stages, about 92% of the chalimus and 74% of the pre-adult females were removed following the use of the fish feed provided by this invention (namely fish feed supplemented with NeemAzal® Technical).

In a second aspect, the invention provides a method of controlling, preventing or treating pest infections or infestations of fish, the method comprising administering to fish in need thereof, a quantity of a fish feed of this invention. The method may find particular application in the prevention and/or treatment of ectoparasite infections and/or infestations, including infections and/or infestations comprising sea lice infections or infestations in wild and/or farmed fish. In methods of this type the fish feed may comprise an agent obtainable from a plant of the genus *Azadirachta*. For example the fish feed may comprise azadirachtin A, NeemAzal® Technical and/or any of the pest control agents described herein.

The methods of this invention may further involve the use of compositions, for example liquid (or aqueous) compositions comprising azadirachtin A, NeemAzal® Technical and/or any of the pest control agents described herein. Compositions of this type may be administered separately to and/or concurrently with, fish feeds of this invention.

It is recognised that different types of treatment can affect the appetite of a fish. Moreover, sick/infested fish and/or less aggressive fish tend to eat less than healthy, dominant fish.

In order to control a pest and overcome the problems associated with loss of appetite through illness, infection and/or infestation, any form of pest control agent as described herein may be added directly to the water as a bath treatment in order to begin treatment and improve appetite. Thereafter, a fish feed of this invention may be administered.

Thus, the invention provides a fish feed comprising azadirachtin A, NeemAzal® Technical and/or any of the pest control agents described herein and a composition comprising azadirachtin A, NeemAzal® Technical and/or any of the pest control agents described herein, for use in controlling, treating and/or preventing a pest infection/infestation of a fish, wherein the feed is intended to be administered together/concurrently with, after and/or separately from the composition.

The invention also provides a method of controlling, preventing and/or treating a pest infection/infestation of a fish, said method comprising administering to a fish in need thereof a composition comprising azadirachtin A, NeemAzal® Technical and/or any of the pest control agents described herein and a feed comprising azadirachtin A, NeemAzal® Technical and/or any of the pest control agents described herein, wherein the composition is administered together/concurrently with, after and/or separately from the feed.

Accordingly, the methods of this invention may exploit compositions and/or fish feeds, which compositions and/or feeds are suitable for fish, including any fish belonging to the various families detailed above, including, for example, those belonging to the family Salmonidae and comprising azadirachtin A, NeemAzal® Technical and/or any of the pest control agents described herein.

It should be understood that fish "in need thereof", may be fish which are infected and/or infested with one or more pests, including, for example, ectoparasites (for example sea lice) or fish which are predisposed and/or susceptible to pest, including ectoparasite, infections/infestations.

The "quantity" of agent to be administered as part of the fish feed (in other words the dose of agent (for example azadirachtin A, NeemAzal® Technical and/or any of the pest control agents described herein)) may be any quantity or dose which is effective at treating or preventing a pest, including ectoparasite, infection/infestation. The administered dose may vary depending on multiple factors such as the fish and/or parasite species, the age of the fish, the water conditions and/or the level of infection.

In a third aspect, the present invention provides a pest control agent (for example an anti-ectoparasite agent) for use in treating and/or preventing pest (ectoparasite) infections and/or infestations in fish. The pest control agent may be administered by applying the agent to a fish feed, as a bath treatment and/or by parenteral administration The pest control agent may comprise azadirachtin A. The pest control agent may comprise or further comprise NeemAzal® Technical and/or any of the pest control agents of the invention. One of skill will appreciate that compositions of this invention comprising azadirachtin A, NeemAzal® Technical and/or a pest control agent of the invention may be formulated for adding to water.

As such, the invention may provide a bath-treatment for fish, said treatment comprising azadirachtin A, NeemAzal® Technical and/or any of the pest control agents described herein.

In view of the above, the present invention also provides azadirachtin A, NeemAzal® Technical and/or any of the pest control agents of the invention for use in treating or preventing sea louse infections/infestations in fish.

The invention may also provide the use of azadirachtin A, NeemAzal® Technical and/or a pest control agent of the invention in the manufacture of a medicament for the treatment and/or prevention of a pest infection/infestation of fish. The medicament of this invention may find particular application in the treatment and/or prevention of ectoparasite infections/infestations in fish. The medicaments of this invention may be exploited in the treatment and/or prevention of sea louse infections and/or infestations in fish belonging to the family Salmonidae.

The pest control agents for use and medicaments of this invention may be administered parenterally, as a bath treatment and/or in feed.

In a fourth aspect, the present invention provides a fish feed according to the first aspect of this invention for use in the treatment and/or prevention of an ectoparasite infection/infestation of fish. The fish feed for use, may comprise azadirachtin A, NeemAzal® Technical and/or any of the pest control agents described herein.

In a fifth aspect, the invention provides a fish feed supplement, wherein said supplement comprises a pest controlling agent of the invention (i.e. of the type described herein). The supplement may be mixed with a fish feed to provide a fish feed of this invention. The supplement may be in solid or liquid form. The supplement may comprise azadirachtin A, NeemAzal® Technical and/or any of the pest control agents described herein.

In a sixth aspect, the invention provides a method of making a supplemented fish feed of this invention, said method comprising the step of mixing a fish feed with one or more of the compositions and/or pest control agents described herein to provide a supplemented fish feed. The method of making a supplemented fish feed of this invention may comprise mixing a fish feed with a quantity of pest control agent such as azadirachtin A, NeemAzal® Technical and/or any of the pest control agents described herein. It should be understood that the fish feed may be a solid feed or a liquid feed. Where the fish feed is a solid feed, the anti-ectoparasite agent may first be mixed with the fish feed to provide a supplemented fish feed, the supplemented fish feed may then be formed into pellets and/or flakes as required.

Additionally or alternatively, a method of making a supplemented fish feed of this invention may comprise the step of providing a fish feed and applying a quantity of pest control agent to a surface of the feed. For example, the method may comprise top coating the feed with a quantity of pest control agent. Where the pest control agent comprises, for example, azadirachtin A, NeemAzal® Technical and/or any of the pest control agents described herein, the method may comprise applying a quantity (for example about 0.1 g to about 1000 g/kg or 0.1 g/kg, 1 g/kg, 2 g/kg, 3 g/kg, 4 g/kg, 5 g/kg, 6 g/kg, 7 g/kg, 8 g/kg, 9 g/kg or 10 g/kg, 20 g/kg, 30 g/kg, 40 g/kg, 50 g/kg, 60 g/kg, 70 g/kg, 80 g/kg, 90 g/kg, 100 g/kg, 250 g/kg, 500 g/kg, 750 g/kg) of azadirachtin A NeemAzal® Technical and/or any of the pest control agents described herein to a surface of a fish feed, for example a fish feed pellet or fish feed flake. The method may further comprise the step of sealing the pest control agent applied to a surface of the fish feed. The pest control agent may be sealed by applying a coat of fish oil to the pest control agent coated fish feed. Any sealing substance used to seal the pest control agent may be applied such that it coats all or a part of the pest control agent coating.

In a seventh aspect, the invention provides azadirachtin A for use in treating or preventing pest infections and/or infestations of fish. The pest infection and/or infestation may be caused or contributed to by an ectoparasite of the type described herein. By way of example, the ectoparasite may be a species of louse (a sea louse for example).

In an eighth aspect, the invention provides NeemAzal® Technical for use in treating or preventing pest infections and/or infestations in fish. The pest infection and/or infestation may be caused or contributed to by an ectoparasite of the type described herein. By way of example, the ectoparasite may be a species of louse (a sea louse for example).

In a ninth aspect, the invention provides an azadirachtin-containing pest control agent for use in treating or preventing pest infections and/or infestations in fish. The pest infection and/or infestation may be caused or contributed to by an ectoparasite of the type described herein. By way of example, the ectoparasite may be a species of louse (a sea louse for example). In one embodiment, the invention provides a fish feed comprising a neem extract for use in treating or preventing pest infections and/or infestations in fish.

In a tenth aspect of this invention, the invention provides a method of treating or preventing a pest infection and/or infestation of a fish, the method comprising administering a quantity of azadirachtin A, NeemAzal® Technical and/or any of the pest control agents described herein to a fish in need thereof. A "quantity" of azadirachtin and/or NeemAzal® may be any quantity effective to treat or prevent the pest infection/infestation. A "fish in need thereof" may be any fish having or suffering from a pest infestation/infection or any fish predisposed and/or susceptible to a pest. The pest may be an ectoparasite. The ectoparasite may be a species of louse (for example a species of sea louse).

It should be understood that the definitions of terms, including the terms "pest", "fish", "azadirachtin", "azadirachtin A", "NeemAzal®", "NeemAzal® Technical", "Margosa Extract" and "neem extract", as used for the first (and other) aspects of this invention apply to the various embodiments of all other aspects of this invention including the second-tenth aspects described above. Accordingly, the pest control agent for use according to the seventh, eighth and ninth aspects of this invention and the method of the second and tenth aspects of this invention may be applied to the treatment and/or prevention of a pest infection and/or infestation of a fish belonging to the family Salmonidae. In addition, the pest control agents for use according to the seventh, eighth and ninth aspects of this invention and the method of the second and tenth aspects of this invention may be applied to the treatment and/or prevention of an ectoparasite (for example sea (salmon) louse: *Lepeophtheirus salmonis*), fungal and/or amoeba infection and/or infestation of a fish belonging to the family Salmonidae.

DETAILED DESCRIPTION

The present invention will now be described in detail with reference to the following Figures which show:

FIG. 1: Development of attached *L. salmonis* over time. Lice challenge cohort II—Day-2.

FIG. 2: Development of attached *L. salmonis* over time. Treatment ends—Day 6.

FIG. 3: Development of attached *L. salmonis* over time. Sample 1—Day 13.

FIG. 4: Development of attached *L. salmonis* over time. Sample 2—Day 28.

FIG. 5: Sub-study A: Lice numbers (all stages) on day 13 (7 days post treatment).

FIG. 6: Sub-study A: Lice numbers (chalimus>pre-adults) on day 13 (7 days post treatment). Results show a ~92% reduction in numbers of chalimus developing to pre-adults.

FIG. 7: Sub-study A: Lice numbers (pre-adults>adults) on day 13 (7 days post treatment). Results show a small reduction in numbers of pre-adults developing to adults.

FIG. 8: Sub-study A: Lice numbers on day 13 (adult male vs all females: 7 days post treatment). The results show a ~74% reduction in pre-adult lice developing to adult females. The results also show that there was little effect on those developing to adult males.

FIG. 9: Sub-study A: Lice numbers (gravid vs non-gravid females) on day 13 (7 days post treatment). Results show that 57% of adult females in control tanks have egg strings and that 5% of adult females in treated tanks have egg strings. This equates to a 98% reduction in egg string production.

FIGS. 10A and B: Sub-study A: Lice numbers on day 28 (3 weeks post treatment). Day 13; A: day 13 pre-adults and adults; B: day 28 adults only.

FIG. 11: Sub-study A: Male lice numbers on day 28 (3 weeks post treatment). Male Lice (including all pre-adults and adults); in the control group, numbers dropped by 35%. In the treated group, numbers dropped by 30%. There were no significant effects to male lice FIG. 12: Sub-study A: female lice numbers on day 28 (3 weeks post treatment). Female Lice (Including all pre-adults and adults); in the control group, numbers dropped by 42%. In the treated group, numbers dropped by 60%. Around 30% of female lice on treated fish on Day 13 have gone by Day 28 relative to controls.

FIG. 13: Sub-study A: Lice (gravid vs non-gravid females) numbers on day 28 (3 weeks post treatment). The results show that 66% of adult females in control tanks have egg strings whereas 13% of adult females in control tanks had egg strings. This equates to a 98% reduction in egg string production.

FIG. 14: Sub-study B part I: Lice (adult male vs females) numbers on day 13 (7 days post treatment). There were no significant differences in numbers of adult male or female lice.

FIG. 15: Sub-study B part I: Lice (gravid vs non-gravid females) numbers on day 13 (7 days post treatment). The results show that 95% of adult females in control tanks had egg strings whereas 3% of adult females in control tanks had egg strings. This equates to a 93% reduction in egg string production.

FIG. 16: Sub-study B part I: Lice (male) numbers on day 28 (3 weeks post treatment). All male lice; in the control group, numbers dropped by 20%. In the treated group, numbers dropped by 27%. There were no significant effects on male lice numbers.

FIG. 17: Sub-study B part I: Lice (female) numbers on day 28 (3 weeks post treatment). All Female Lice; in the control group, numbers dropped by 48%. In the treated group, numbers dropped by 77%. The differences are not statistically significant due to tank-to-tank variability FIG. 18: Sub-study B: Lice (gravid vs non-gravid females) numbers on day 28 (3 weeks post treatment). The results show that 97% of adult females in control tanks have egg strings whereas 7% of adult females in control tanks have egg strings. This equates to a 96% reduction in egg string production.

FIG. 19: Sub-study B part II: Day 36, 7 days post challenge, 4 weeks post treatment.

FIG. 20: Sub-study B part II: Day 36, 7 days post challenge, 4 weeks post treatment.

The results show that there is no significant reduction in adult male or female numbers.

FIG. 21: Sub-study B part II: Day 36, 7 days post challenge, 4 weeks post treatment. Gravid vs non-gravid females; The results show that 94% of adult females in control tanks have egg strings whereas 88% of adult females in treated tanks had egg strings. There is no significant reduction.

FIG. 22: Sub-study B part II: Day 55, 3 weeks post challenge, 7 weeks post treatment. Males vs females; there is no significant reduction in adult male or female numbers.

FIG. 23: Sub-study B part II: Day 55, 3 weeks post challenge, 7 weeks post treatment.

FIG. 24: Sub-study B part II: Day 55, 3 weeks post challenge, 7 weeks post treatment. Gravid vs non gravid females; the results show that 88% of adult females in control tanks have egg strings whereas 84% of adult females in treated tanks had egg strings. There is no significant reduction.

FIG. 25: Is a chart showing the numbers of attached sea lice per fish.

FIG. 26: Is a chart showing percent of females having egg strings.

EVALUATION OF EFFICACY OF NEEMAZAL® AGAINST SEA LICE (*Lepeophtheirus salmonis*) INFECTING ATLANTIC SALMON The following represents the results of a major trial of the effect of the pest control agent (i.e. NeemAzal®) added to fish feed, on and *Lepeophtheirus salmonis* infections/infestations in Salmonidae. The trial was performed at an accredited research institute and demonstrates the efficacy of azadirachtin-containing pest control agents on the treatment of sea louse in salmon. However in commercial use the dosages, treatment time, and period of protection are indicative only and will vary by a number of factors including, but not limited to: fish species, whether used in fresh or sea water, water temperature, target pest, feeding behaviour, and environmental conditions.

Aims

To evaluate the efficacy of NeemAzal® Technical against different sea louse life stages as follows:
1. Effect of therapeutic treatment on numbers of gravid lice, egg production and egg viability
2. Effect of therapeutic treatment on numbers of chalimi and pre-adult lice
3. Effect of prior treatment on attachment and development of copepodids through chalimus stages
4. Effect of prior treatment on re-infection by motile lice Materials and Methods 2 sub-studies A & B in parallel
Temperature 12-15 degrees C.
Sea lice produced in lab culture
Fish infected with copepodids using experimental challenge model
Lice allowed to develop to required stage
Dosed by voluntary feeding for 7 days
Fish anaesthetised or killed and examined for lice (numbers and stages)
Fillet samples for chemical analysis Dosing Target 25 mg NeemAzal® per kg/day for 7 days
Equivalent to approx. 10 mg azadirachtin A per kg/day
Administered using a feeding rate of 0.5% biomass
Test diet top-coated using 5 g of NeemAzal® per kg feed (0.5% w/w), sealed with fish oil
Hand fed, 2-4 meals per day
Uneaten feed collected to estimate actual intake
Rations adjusted daily to compensate for uneaten feed on previous day
Sub-study A
Treatment of fish already infected with chalimus and pre-adult stages
Evaluated effect on numbers of chalimi and pre-adults at 1 week and 3 weeks post-treatment
Evaluated effect on sea louse egg production and viability

TABLE 1

Timeline for sub-study A

| Day | Procedure |
| --- | --- |
| −26 | Copepodid challenge (cohort 1) |
| −12 | Fish randomly allocated to 6 experimental tanks (41 fish/tank) |
| −4 | Copepodid challenge (cohort II) |
| −1 | Batch weigh (mean 343 g) |
| 0 | First day of test diets |
| 6 | Last day of test diets |
| 13 | 1 week post treatment sample. 20 fish/tank killed and sampled |
| 28 | 3 week post treatment sample. Remaining fish/tank killed and sampled |

TABLE 2

Sub-study A: estimated dose achieved

| Diet | Group | Mean ration consumed (% biomass/day) | Mean dose (mg/kg/day) |
| --- | --- | --- | --- |
| Control | A1 | 0.5 | 0 |
| Control | A2 | 0.49 | 0 |
| Control | A3 | 0.51 | 0 |
| NeemAzal ® | B1 | 0.42 | 20.79 |
| NeemAzal ® | B2 | 0.43 | 20.26 |
| NeemAzal ® | B3 | 0.45 | 22.71 |

Sub-study B

Part I: to determine the effects of therapeutic treatment on attached adult lice
Part II: to determine the effects of prophylactic treatment on copepodid settlement and development, susceptibility to re-infection with motile lice, and egg production and development in adult female lice Sub-study B: Part I To establish effects of therapeutic treatment on adult lice
Fish infected with one cohort of lice
Lice developed to adults and began egg production
Fish were treated for seven days Lice numbers and stages (male, gravid/non gravid female) were determined at 1 and 3 weeks post treatment Sub-study B: Part II To determine efficacy at 3 weeks post treatment against copepodid settlement and adult re-infection Adults from part I were removed Fish were challenged again with copepodids and adult lice at 3 weeks post treatment Lice were sampled after 7 days and 3 weeks (4 weeks and 7 weeks post treatment)

TABLE 3

Timeline for sub-study B

| Day | Procedure |
|---|---|
| −41 | Fish randomly allocated to experimental tanks |
| −37 | Copepodid challenge (cohort 1) |
| −24 | Batch weigh (mean 394 g) |
| 0 | First day of test diets |
| 6 | Last day of test diets |
| 13 | 1 week post treatment sample. 20 fish/tank sampled, lice removed and fish moved to new tanks for use in part II |
| 27 | 3 week post treatment sample. 20 fish/tank sampled and subsequently terminated. |
| 28 | Part II: challenge with copepodids and adult lice |
| 36 | 4 weeks post treatment sample. All fish sampled, adult lice only removed, fish returned to tanks |
| 55 | 7 weeks post treatment sample. Remaining fish killed and sampled |

TABLE 4

Sub-study B: estimated dose achieved

| Diet | Group | Mean ration consumed (% biomass/day) | Mean dose (mg/kg/day) |
|---|---|---|---|
| Control | A1 | 0.48 | 0 |
| Control | A2 | 0.49 | 0 |
| Control | A3 | 0.49 | 0 |
| NeemAzal ® | B1 | 0.48 | 24.46 |
| NeemAzal ® | B2 | 0.49 | 24.20 |
| NeemAzal ® | B3 | 0.48 | 24.03 |

Discussion

The present invention will now be described in detail with reference to the results of a major trial of the active ingredient added to feed.

In summary: the experiment consisted of six tanks each of twenty salmon, three control ("A") and three treatment tanks ("B").

Fish in experimental tanks were fed fish pellets treated with NeemAzal® so that they received, on average, 25 mg of NeemAzal®/kg body weight/day for 7 days, after which they were fed on untreated fish food. Controls received only untreated food.

Three challenges with lice were made: in the first (FIGS. 1-13) the challenge was with immature lice, and in the second, only adults were used (FIGS. 14-18); the third challenge was with immature and mature lice 3 weeks after treatment (FIGS. 19-24).

The first challenge was intended to follow effects on development, the second challenge studied the effects of NeemAzal®-treated fish feed on adult lice especially concerning female fecundity, and the last challenge was aimed to study the loss of effectiveness of the active ingredients with time.

At intervals throughout the experiment, attached lice were counted, and numbers of immature and adult lice and their sex were established. The fecundity of the females was determined by the presence of egg strings.

FIGS. 1-4 show the progression of the lice through their developmental stages in the course of the trial over 4 weeks, starting from a mixture of chalimus and pre-adult stages, with only adults after 28 days.

Sub-study A: Key Findings at 7 Days Post-treatment

92% of chalimus (to pre-adult) removed in test group compared with control

74% of pre-adult females (to adult) removed

Little effect on pre-adult males (to adult)

Egg production in female lice decreased by 98% as a result of reduction in numbers of females and a reduction in the proportion of gravids Few eggs that were produced in test group seemed to hatch and develop normally FIG. 5 represents the total number of lice, of both sexes, at all stages of development, attached to fish, 7 days after treatment. Breaking this down to male and female, both sexes are reduced by 92% in the pre-adult stages. Adult lice numbers, although reduced, are not statistically different from the controls.

FIG. 6 presents the numbers of chalimus stages progressing to pre-adult 7 days after treatment. The figures indicate a 92% reduction (as stated above) in the number of lice at chalimus stage able to develop into pre-adults.

FIG. 7 presents the numbers of pre-adult lice progressing to adult 7 days after treatment. The results indicate no significant effect of the active ingredient treatment in male lice proceeding from pre-adult to adult stage, but there was a significant reduction of 76% in female adult lice.

FIG. 8 represents the numbers of adult male and female lice 7 days after treatment. The numbers summarise the above findings, and emphasise that the development of females to adult stage is severely restricted.

FIG. 9 represents the numbers of gravid and non-gravid females 7 days after treatment. In control fish, the number of gravid females is an average of 57% of the total females, while in the fish fed with the feed of the invention, the number of gravid females has fallen to 5%. Taking into account the reduced number of female lice in the treated fish, this means a reduction of 98% in the egg strings.

Sub-study A: Key Findings at 3 Weeks Post-treatment

Still no effect on numbers of male lice

More female lice had been lost in the test group than in the control group

Egg production was still inhibited in the test group

Eggs that were produced in the test group developed normally

Figure 1:
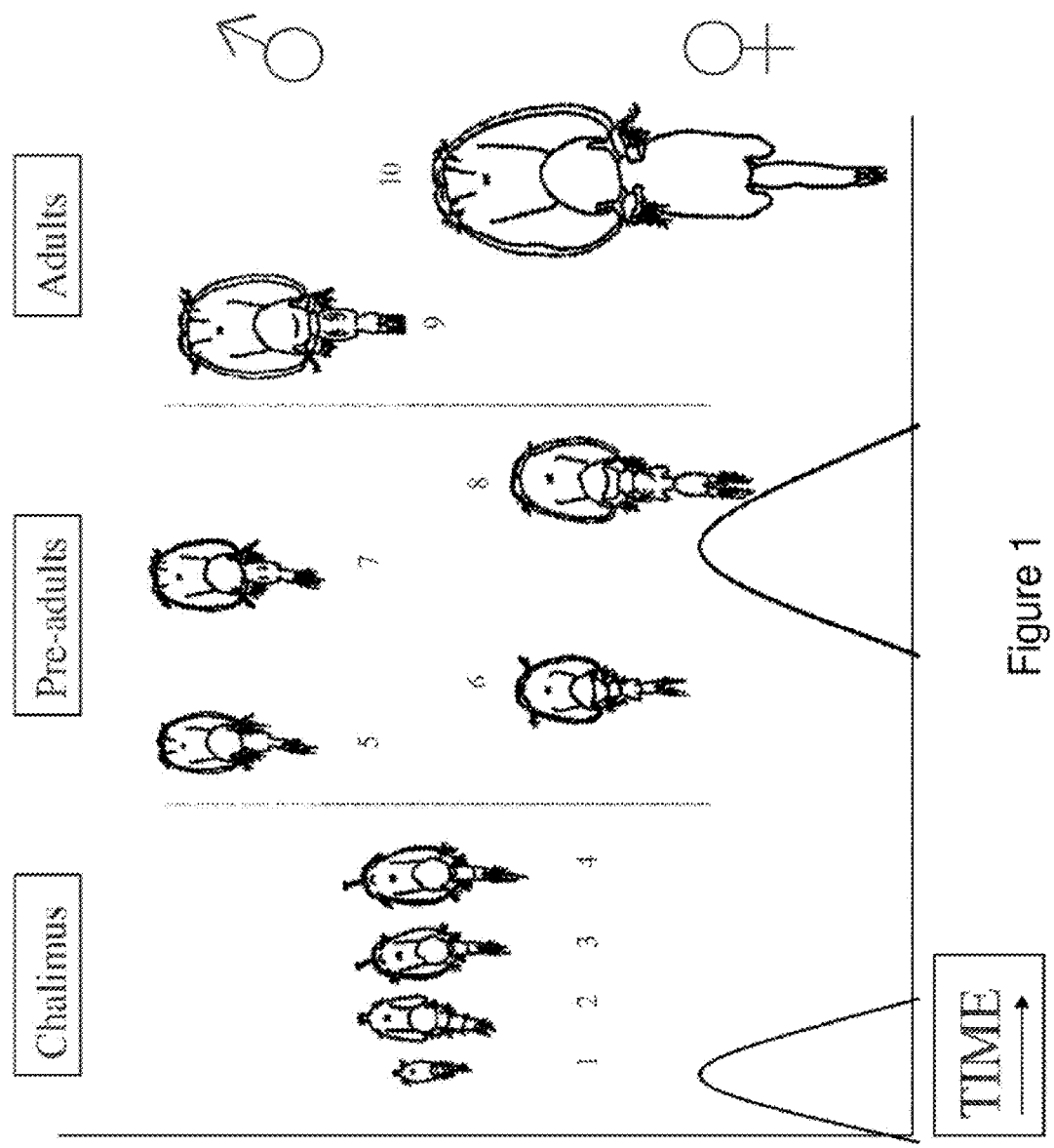
Figure 2:
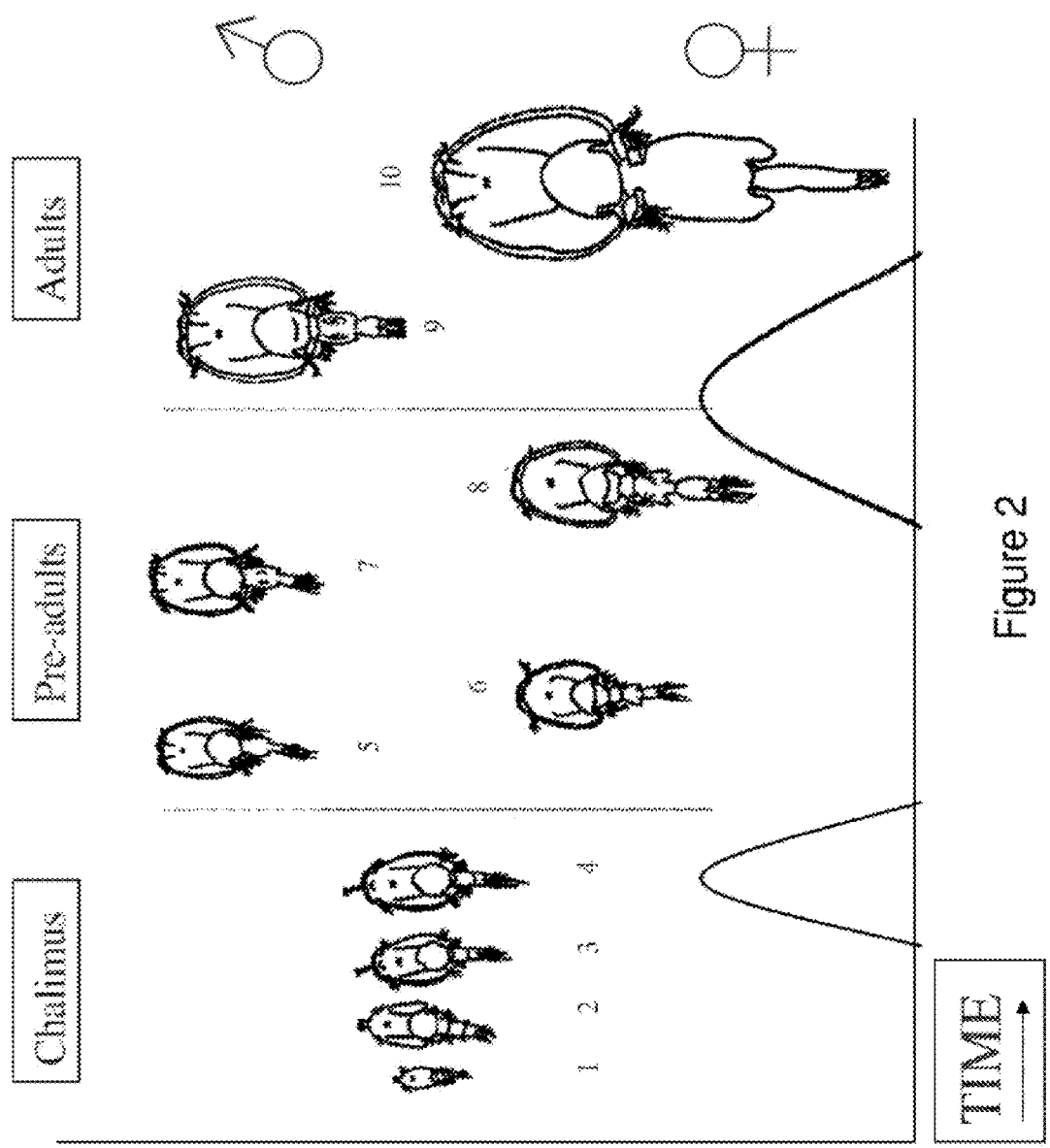
Figure 3:
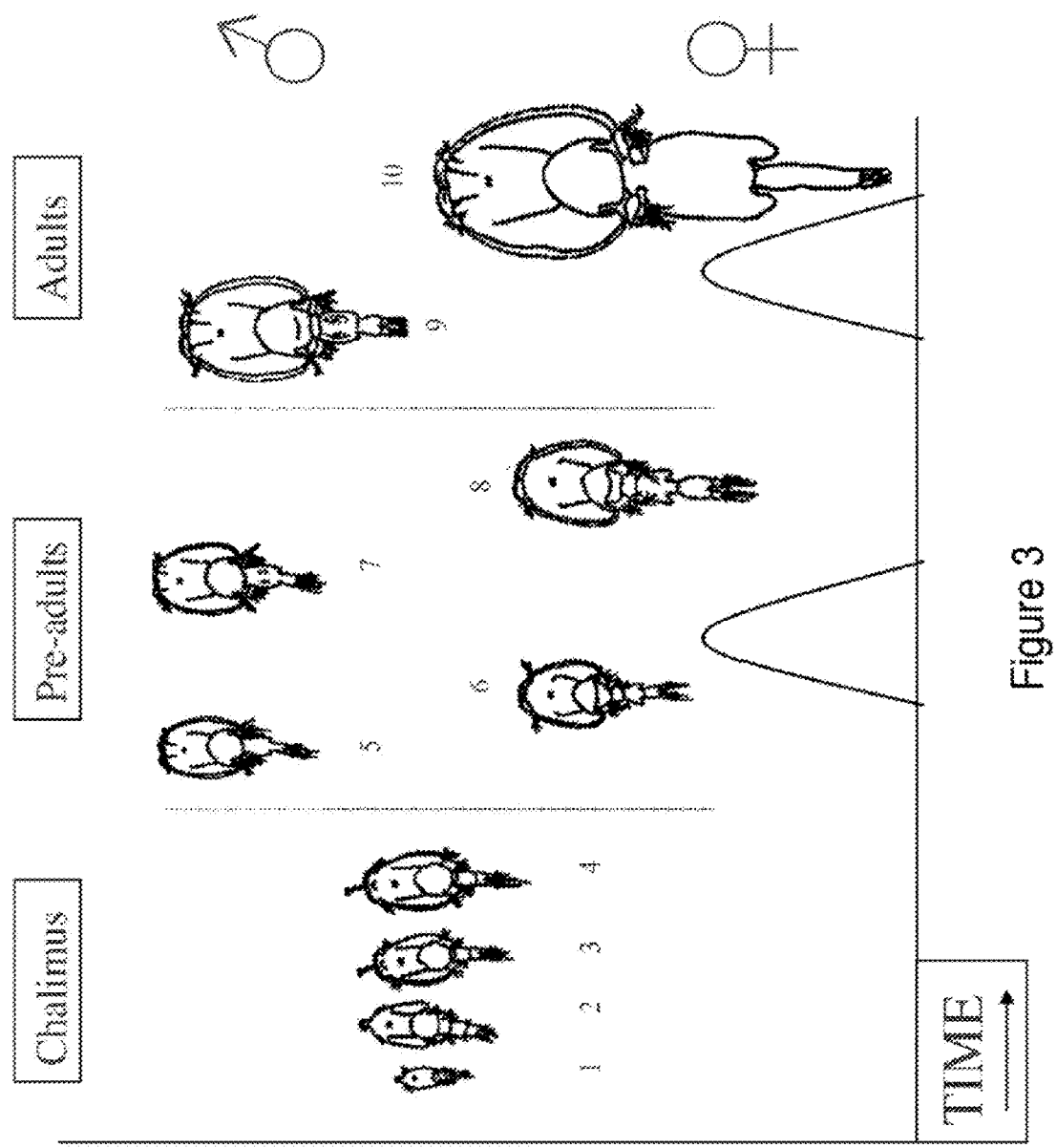
Figure 4:
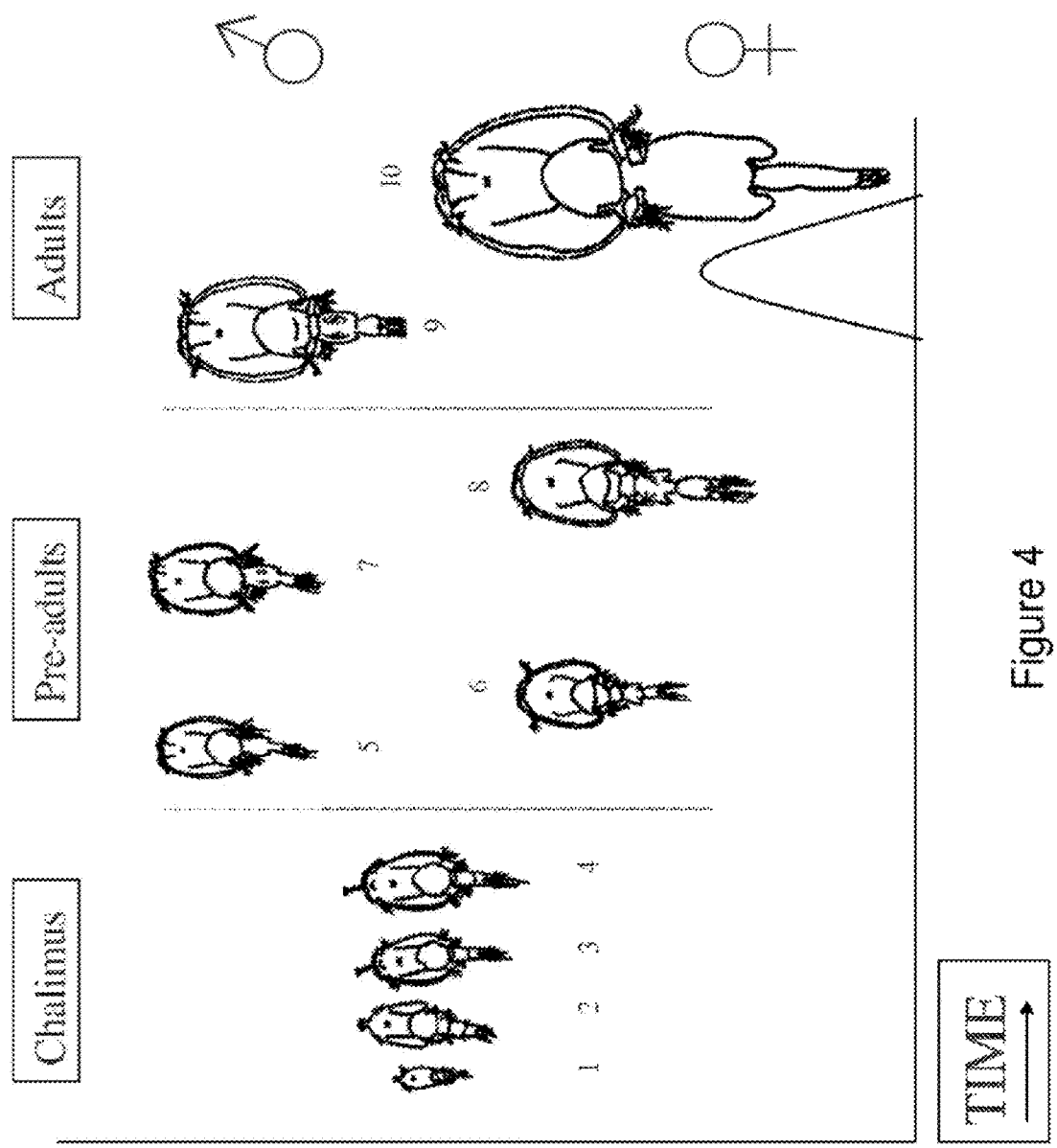
Figure 5:
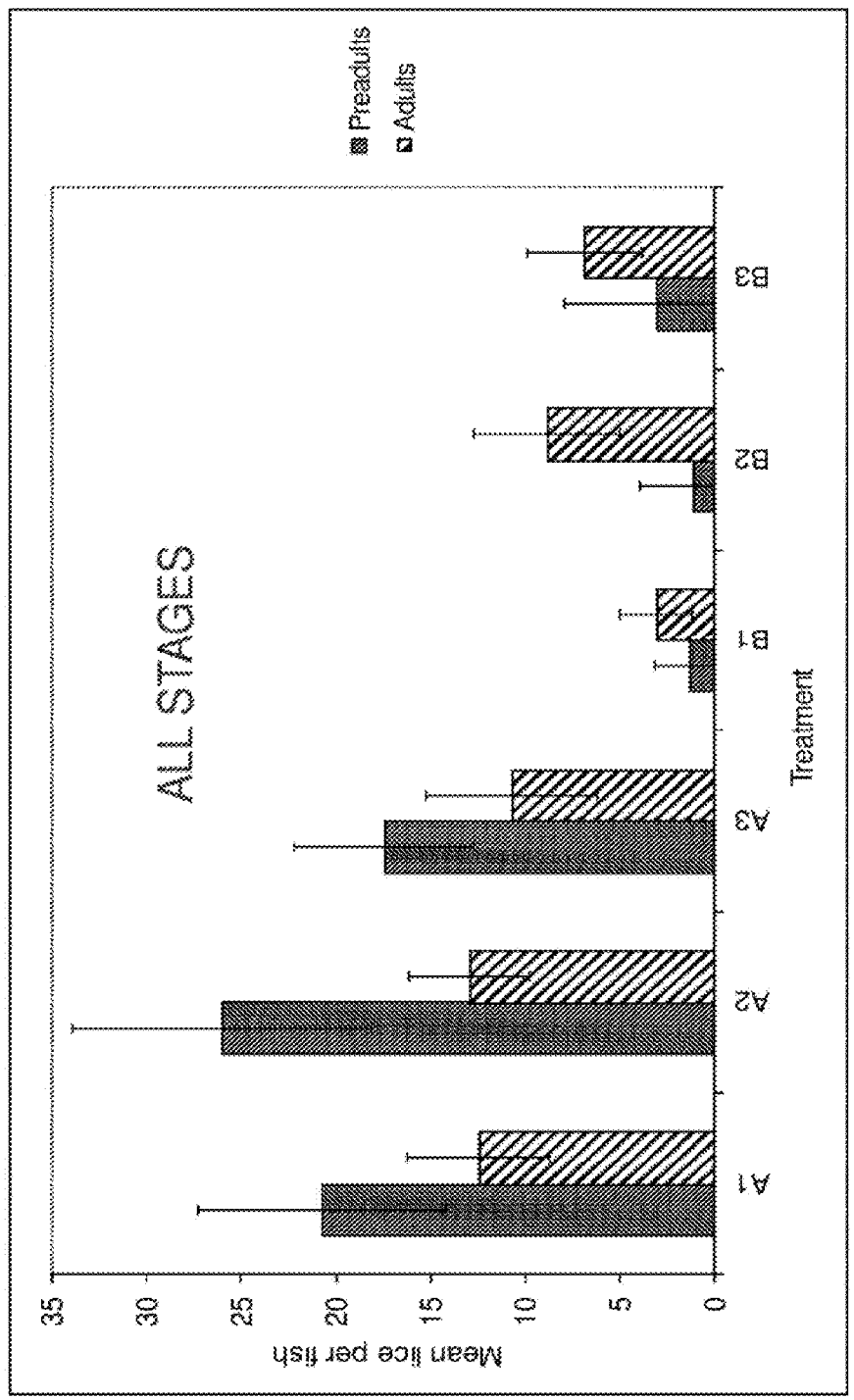
Figure 6:
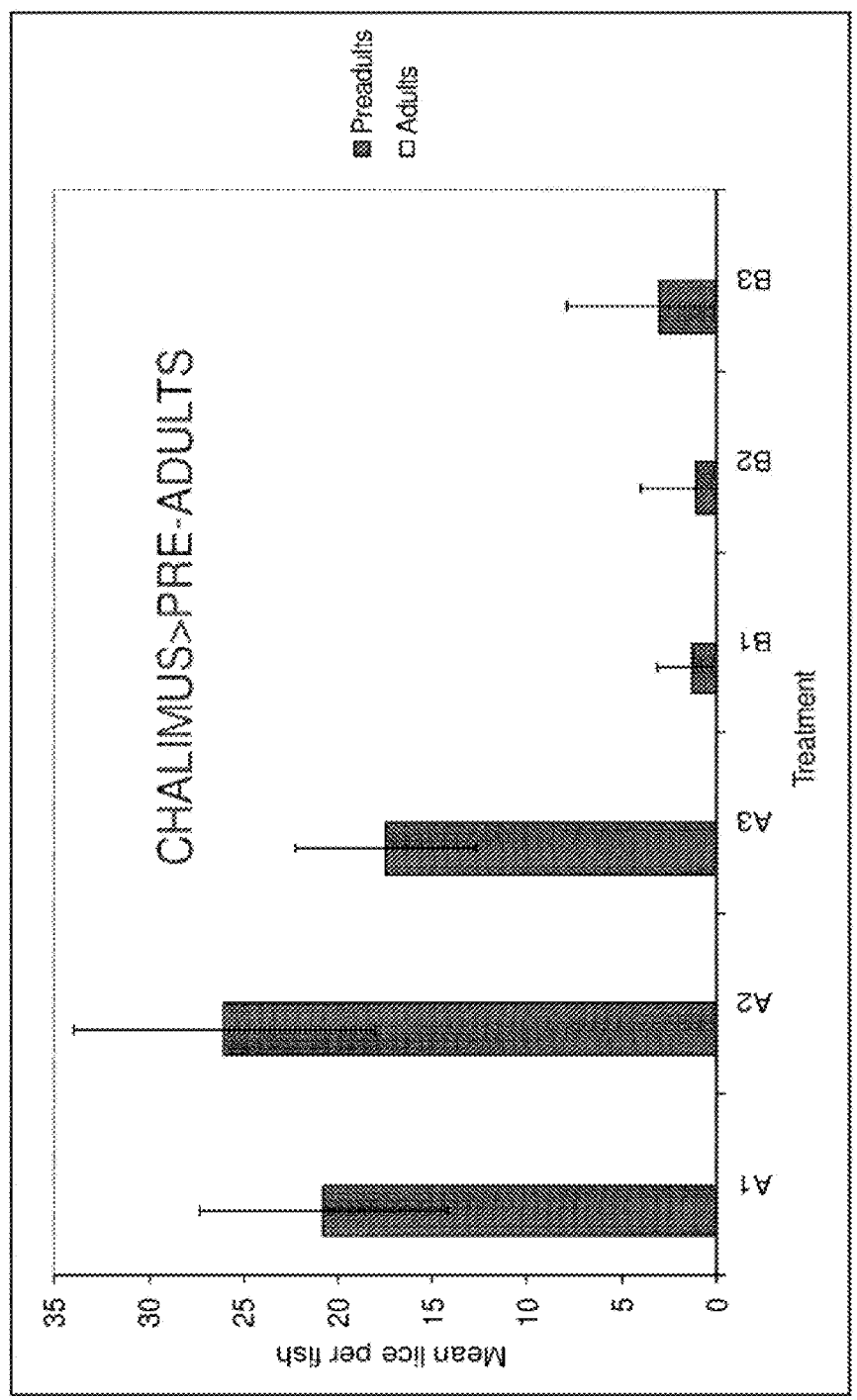
Figure 7:
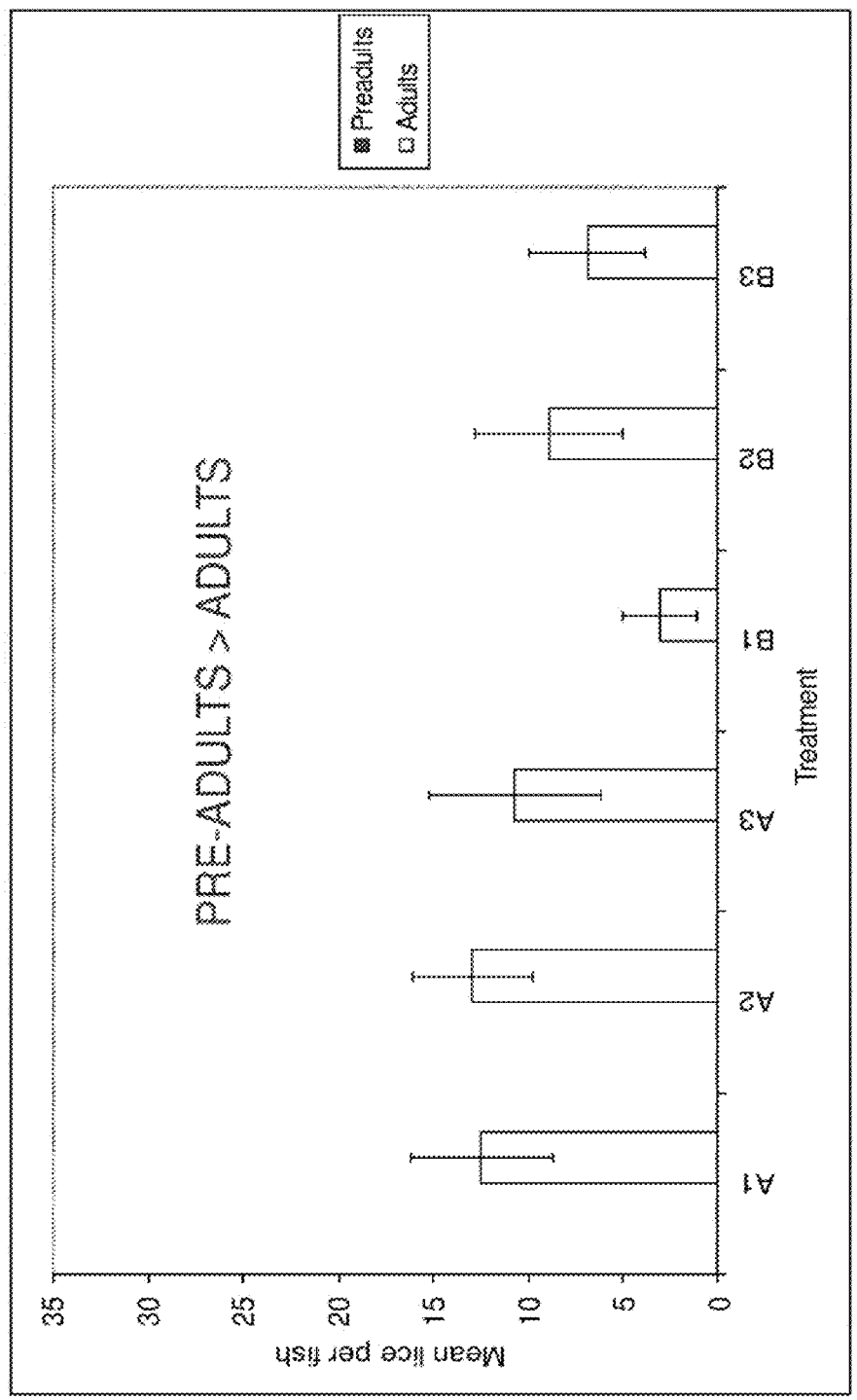
Figure 8:
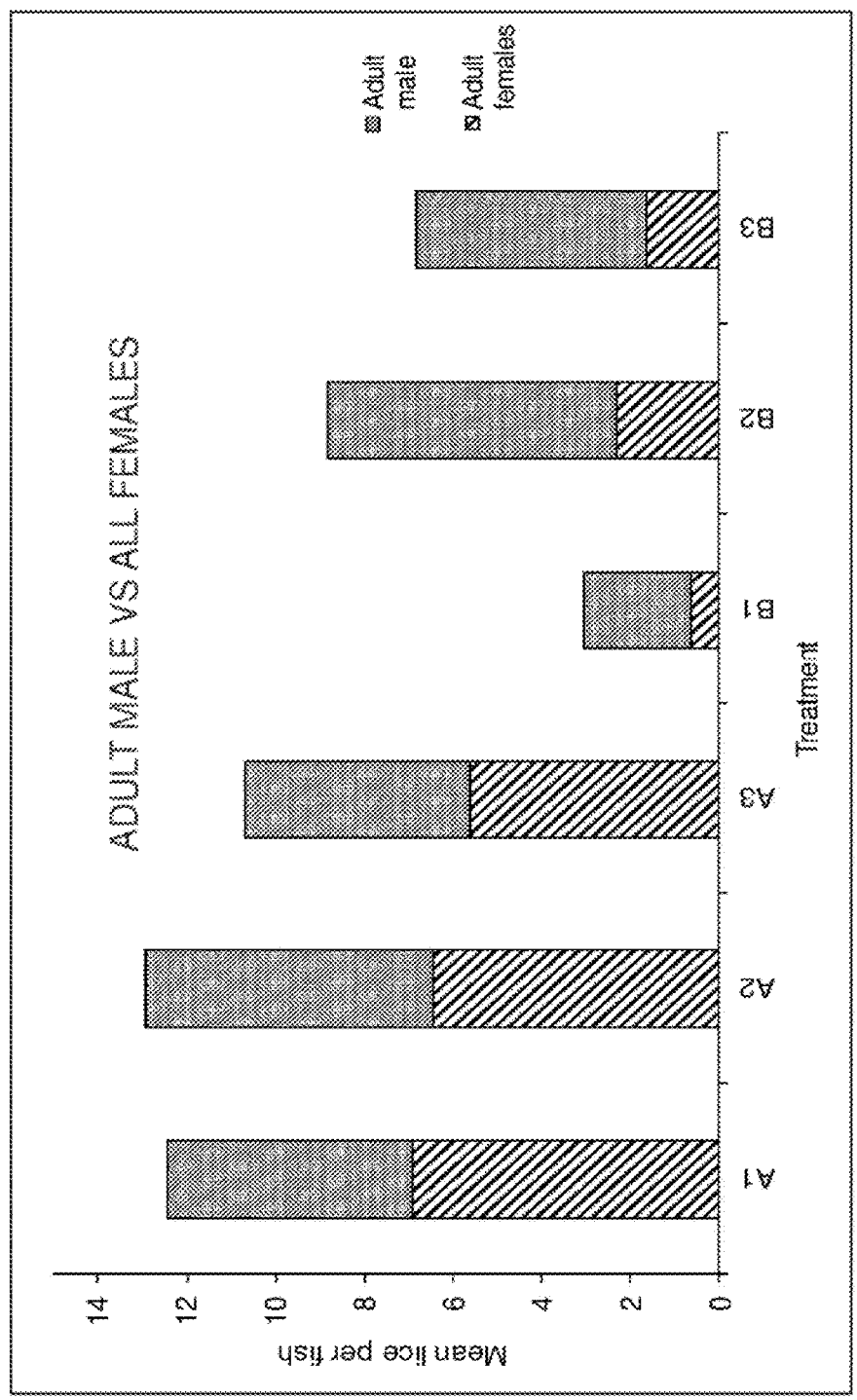
Figure 9:
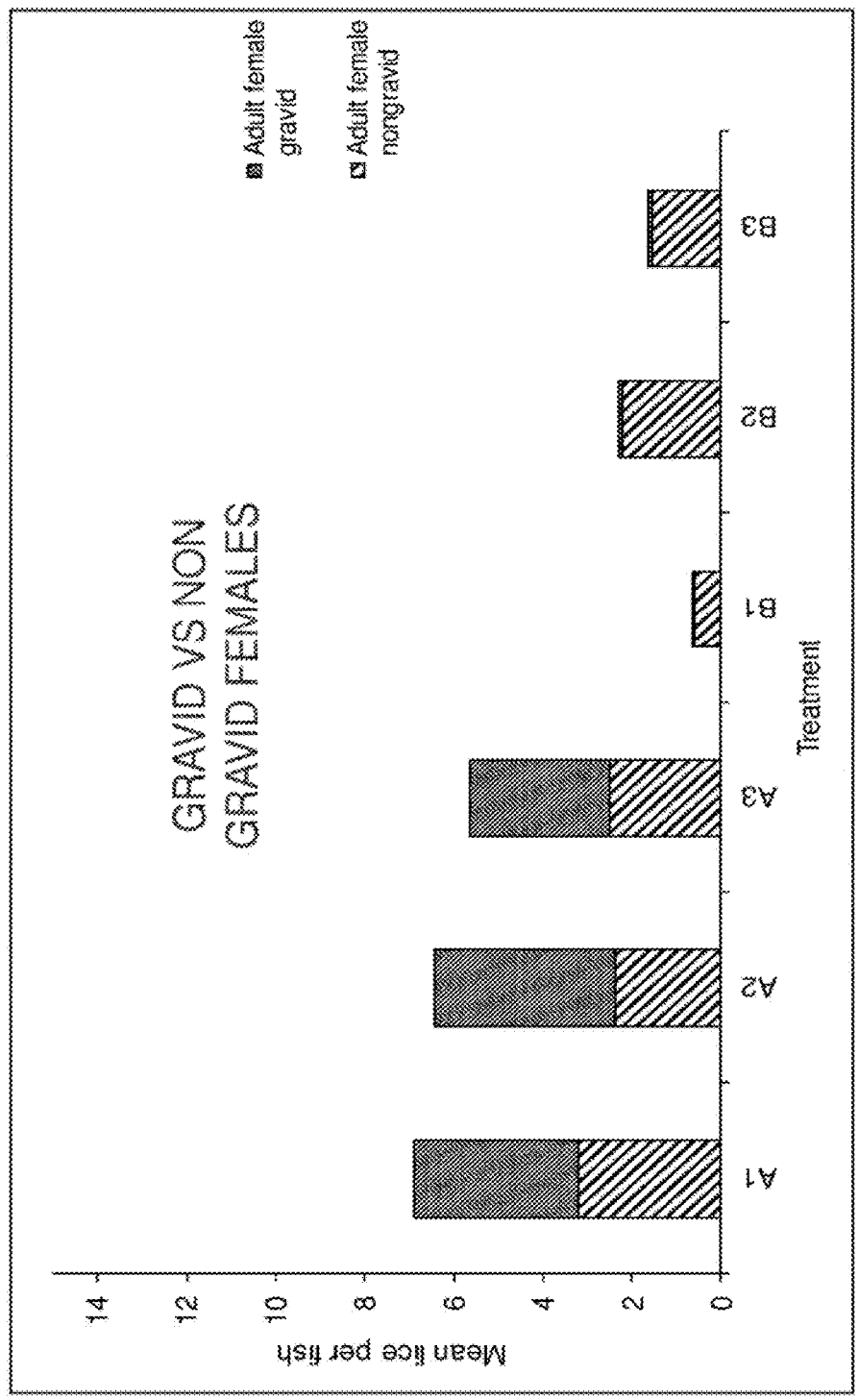
Figure 10:
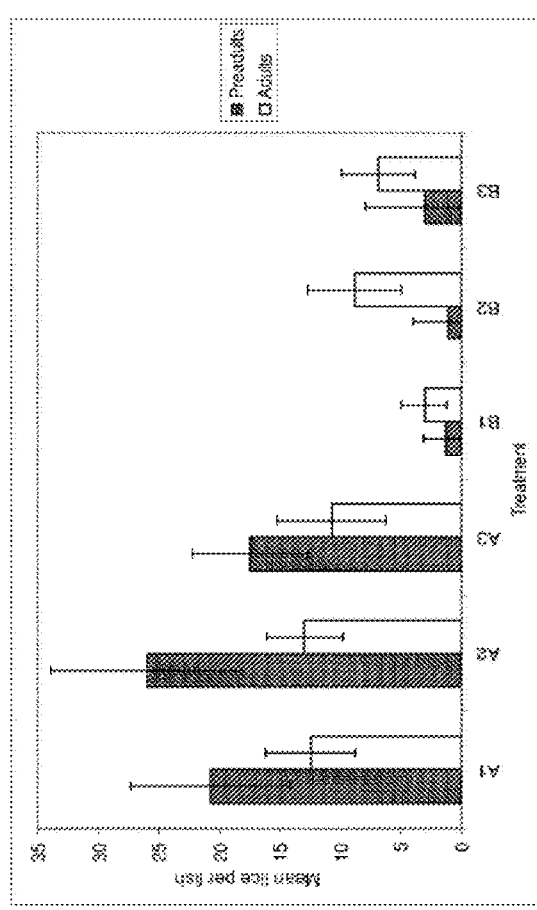
FIG. 10 represents the total numbers of lice 7 days after treatment (A) and 21 days after treatment (B). 3 weeks after treatment had ceased there were only adults present on the fish in contrast to the numbers at 7 days, where most lice were in immature stages. The treatment with the feed of the invention had reduced the numbers of surviving adults of both sexes by 87%.
Figure 10:
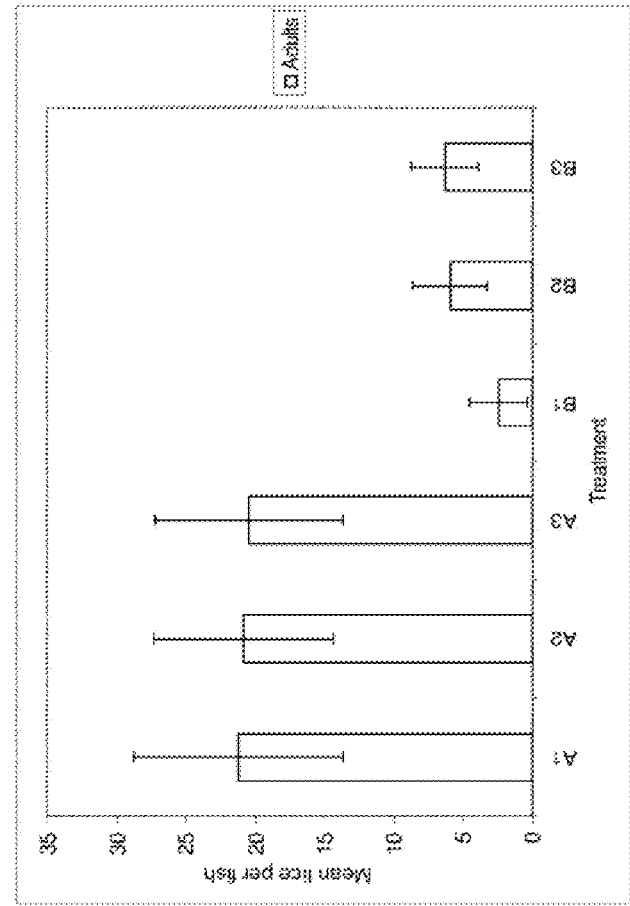
Figure 11:
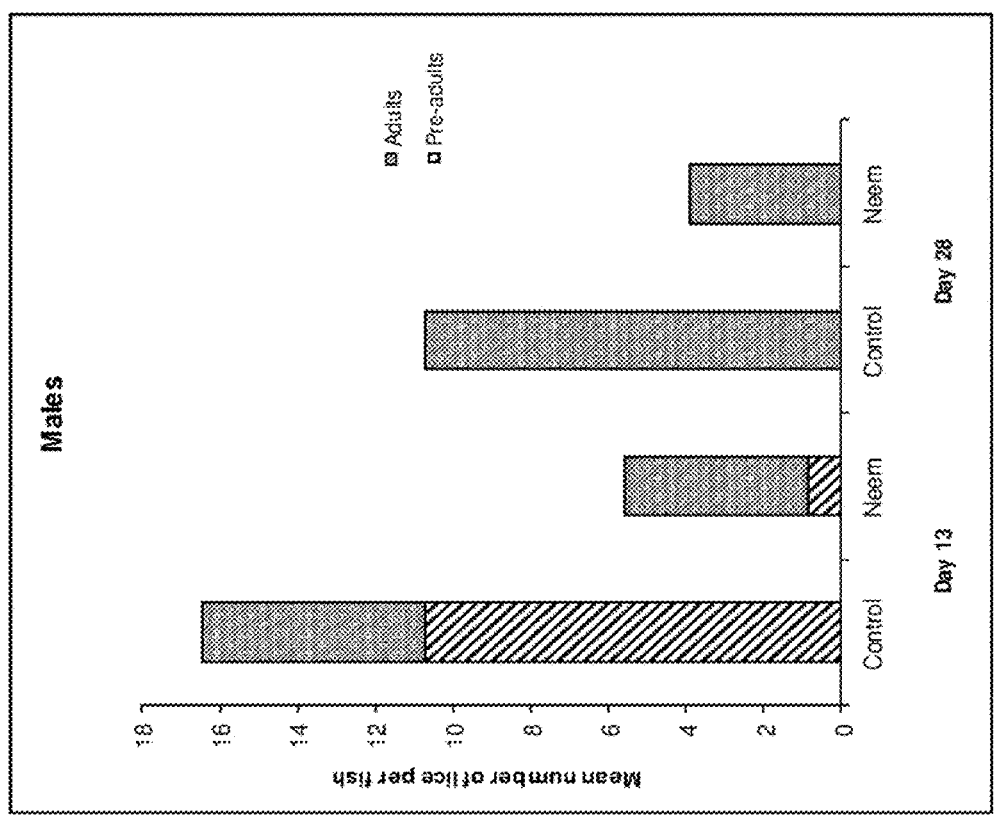
FIGS. 11 and 12 show the results of FIG. 10 broken down by sex 3 weeks after the treatment had ceased, the number of adult males was reduced by 64% compared to controls, while the number of surviving females was reduced by 90% compared to the controls.
Figure 12:
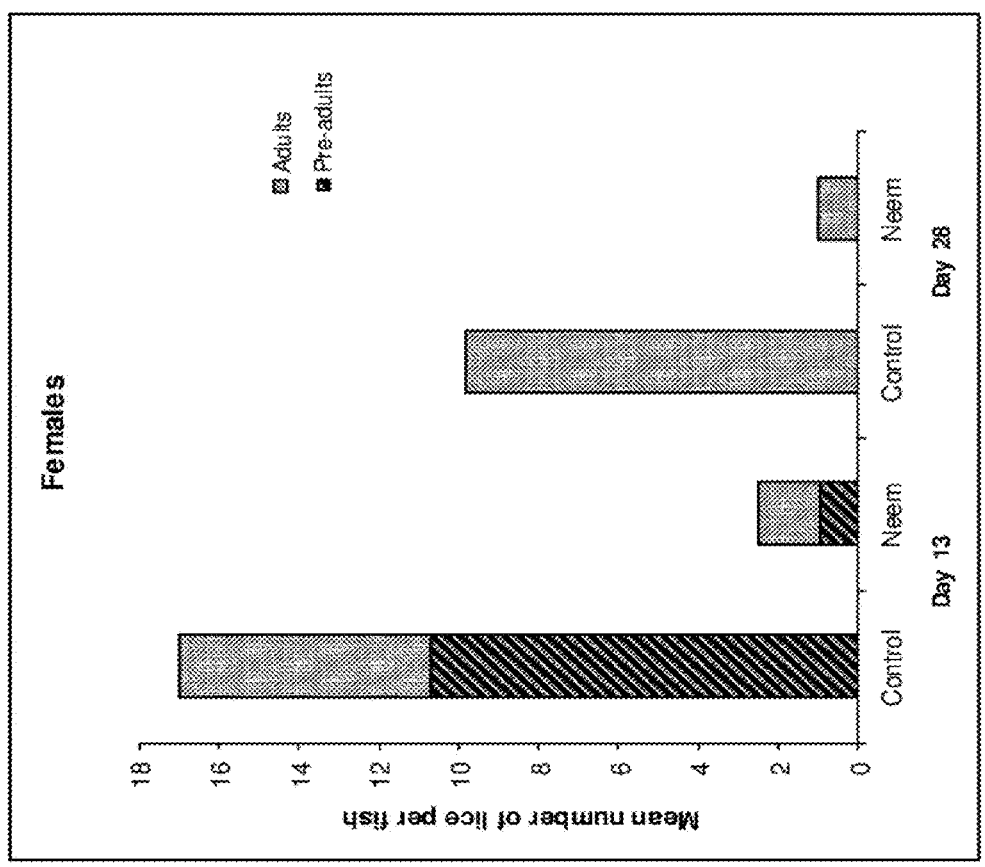
Figure 13:
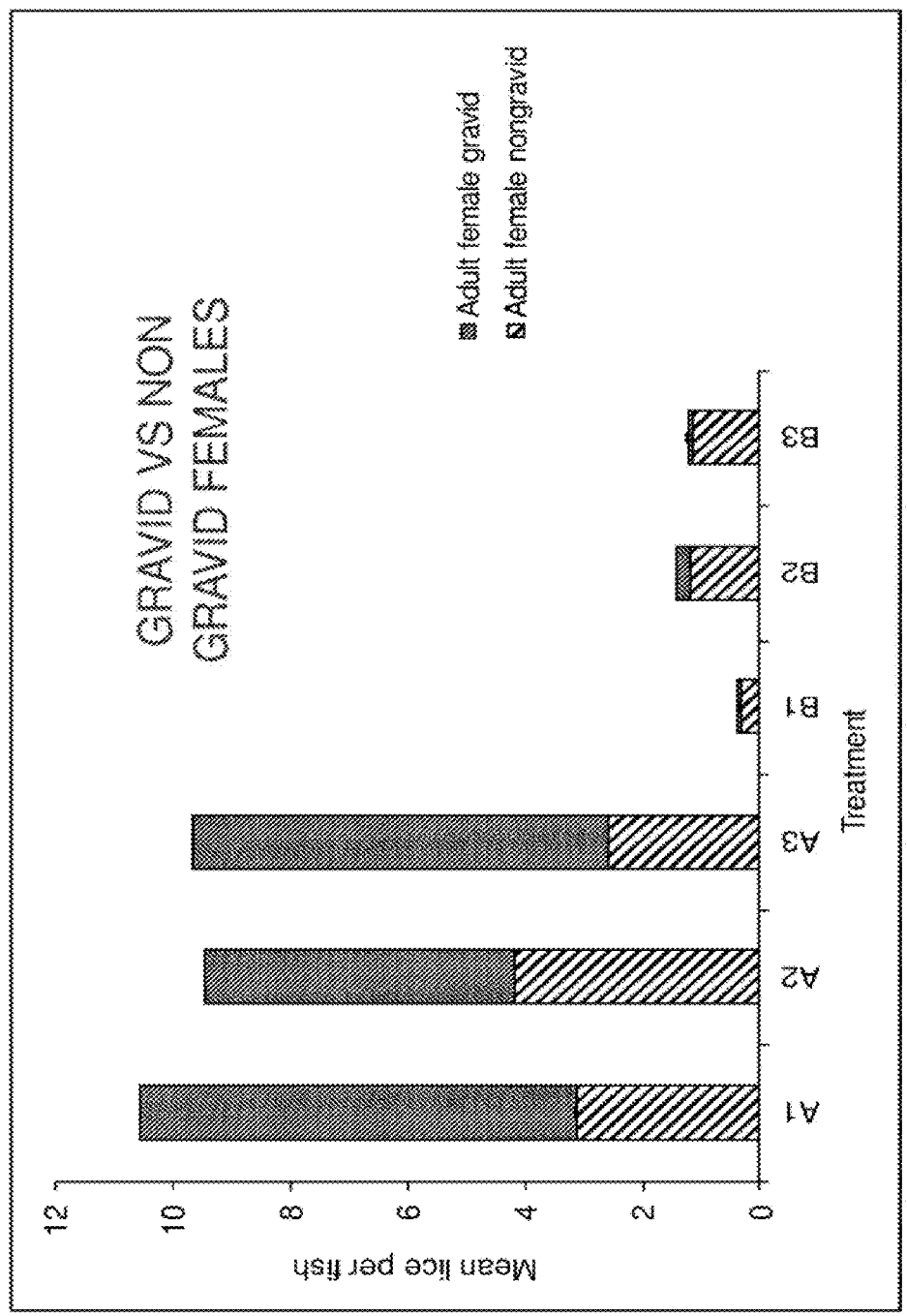

FIG. 13 shows the number of gravid females 3 weeks after treatment. Not only were the total numbers of females reduced by 90% as a result of the treatment with the feed of the invention, but also almost none of the survivors were gravid: 12% compared to 66% in control fish. Overall, control fish produced a total of 884 egg strings, while treated fish produced only 16 egg strings, a reduction of 98% in the number of strings.

Sub-study B Part I: Key Findings on Day 13 (7 Days Post Treatment)

No significant reduction in adult male or adult female lice numbers

93% reduction in the number of egg strings produced

Eggs that were produced developed normally

Figure 14:
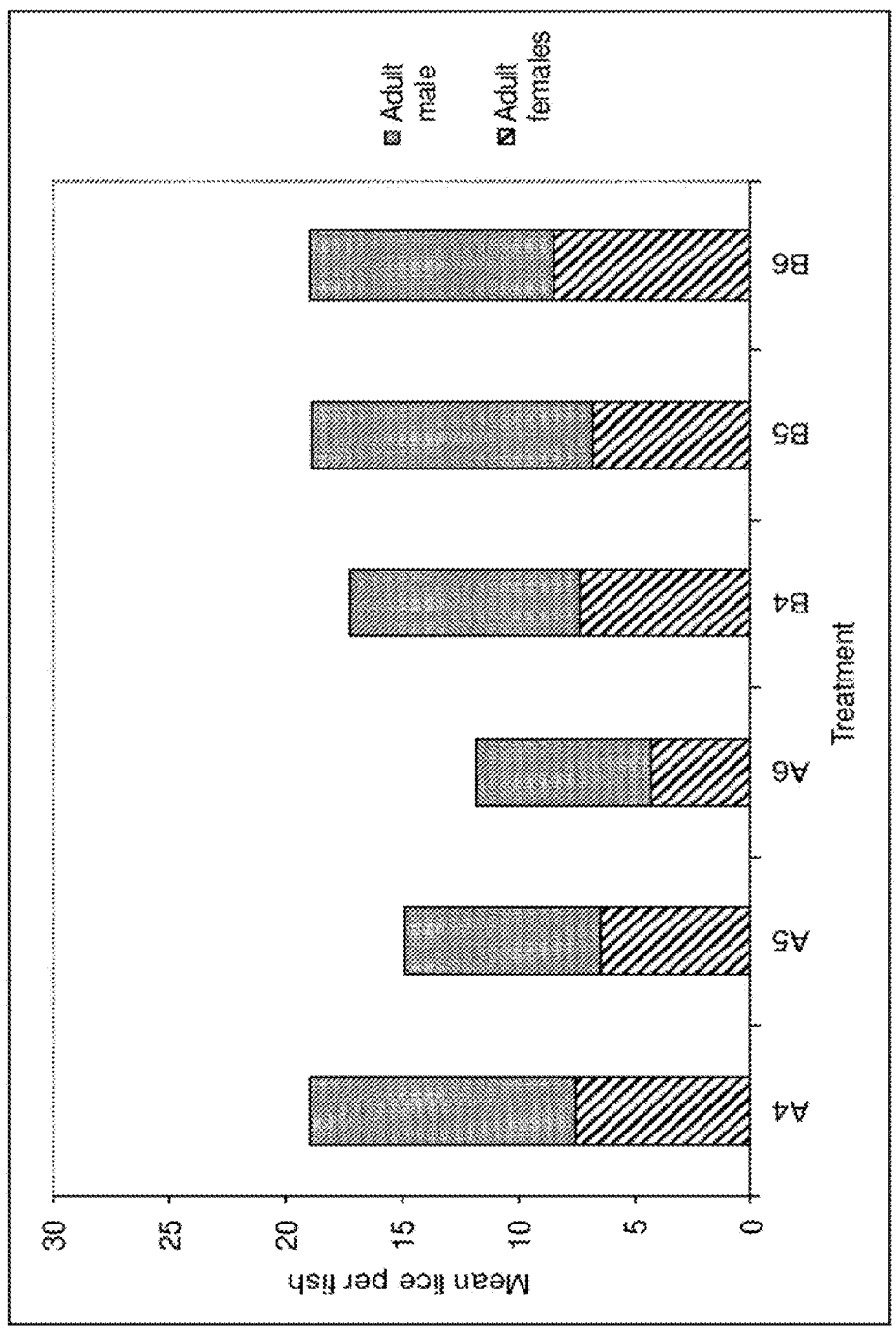

FIG. 14 presents the numbers of lice 7 days after treatment, following an infestation by adult lice only. When the infestation was only induced with adult lice, there was no significant mortality of lice 7 days after treatment, indicating that, as was expected from insect studies, the active ingredient has its main effect in disrupting the developmental process.

Figure 15:
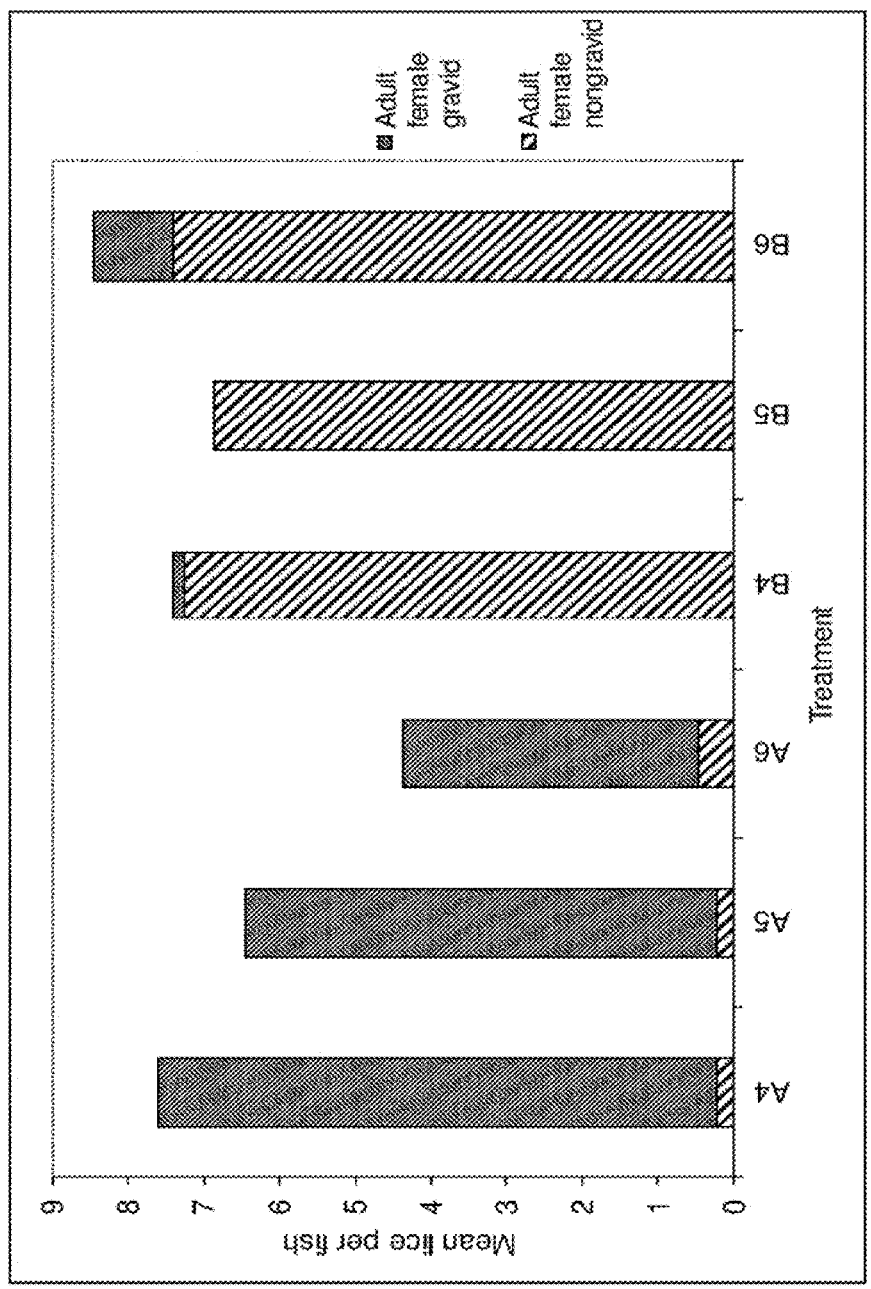

FIG. 15 presents the numbers of gravid females 7 days after treatment. While 95% of the control females had egg strings, only 3% of the active ingredient-treated females were gravid, a reduction of 93% in egg string production. This shows that the anti-fecundity effect of the active ingredient-comprising diet affected mature females.

Sub-study B Part I: Key Findings On Day 28 (3 Weeks Post Treatment)

No significant effect on numbers of adult males and female

Continued effect on ovigerous females, still no egg production

Figure 16:
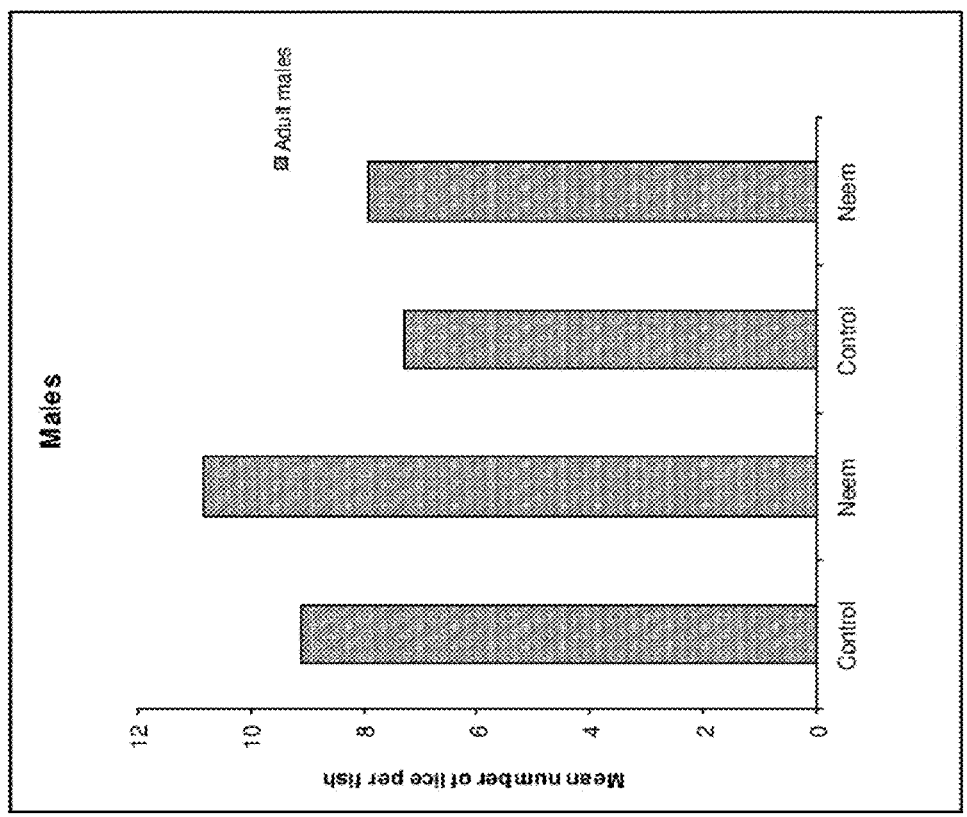
Figure 17:
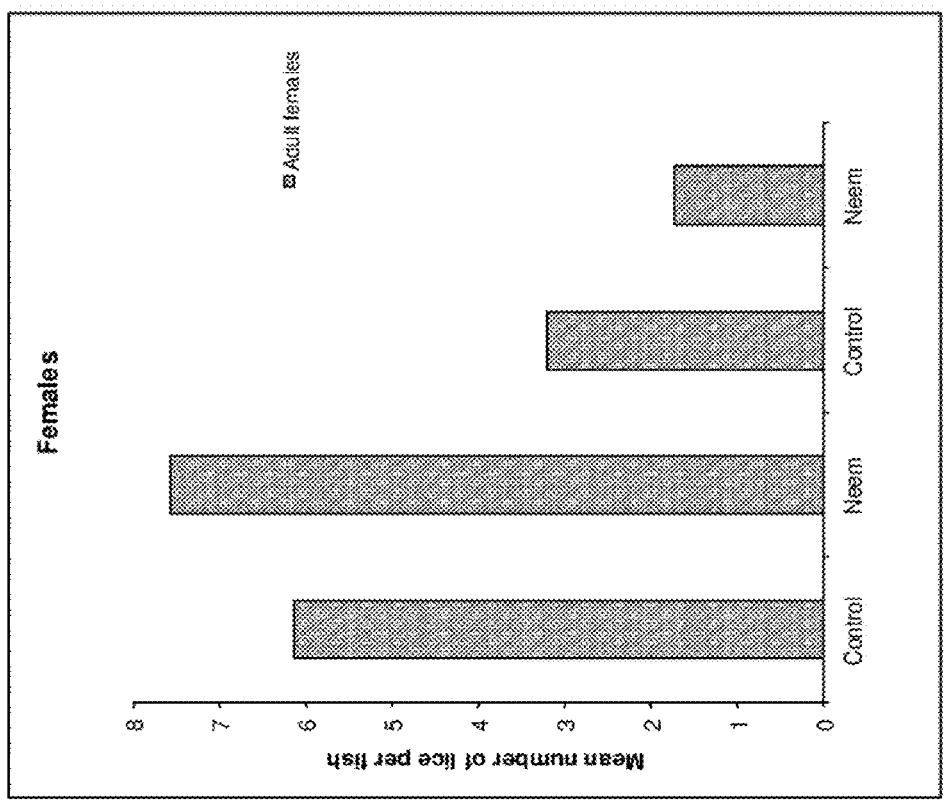

FIGS. 16 and 17 present the numbers of male and female lice 13 and 28 days after treatment. There was no reduction of numbers of mature males as result of the active ingredient-comprising diet. Although there was an apparent reduction in female numbers it was not statistically significant due to differences between tanks.

Figure 18:
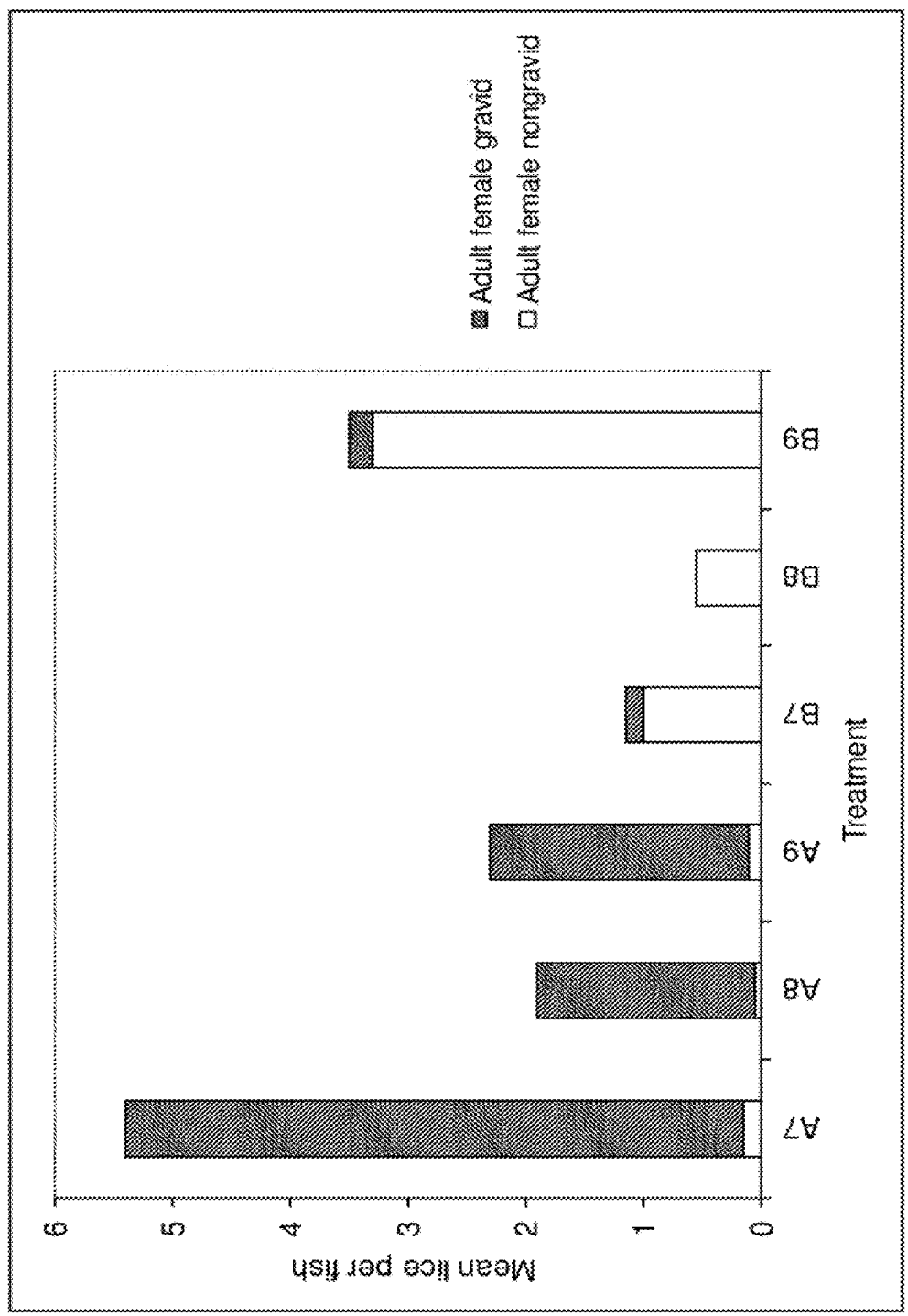

FIG. 18 represents the fecundity of female lice 3 weeks after treatment. The results show that the effect of the active ingredient-comprising diet is still present after three weeks, as the depletion of egg string production equates to 96%.

Sub-study B Part II: Key Findings

No prophylactic effect against numbers of attached chalimus (challenge 3 weeks post-treatment at 12-15 degrees C.)

No prophylactic effect against numbers of adults (males or females)

No prophylactic effect on egg production

Figure 19:
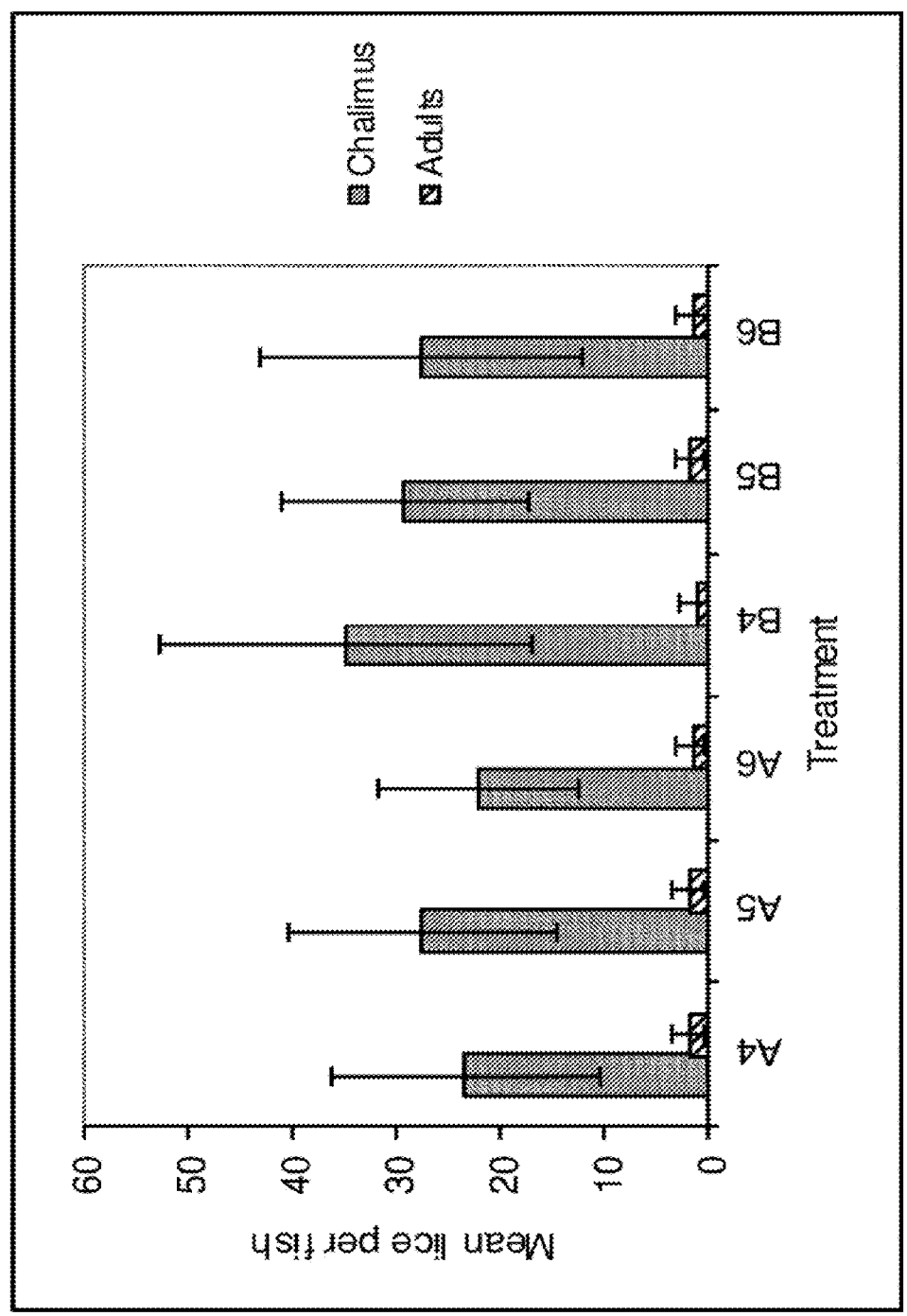
Figure 20:
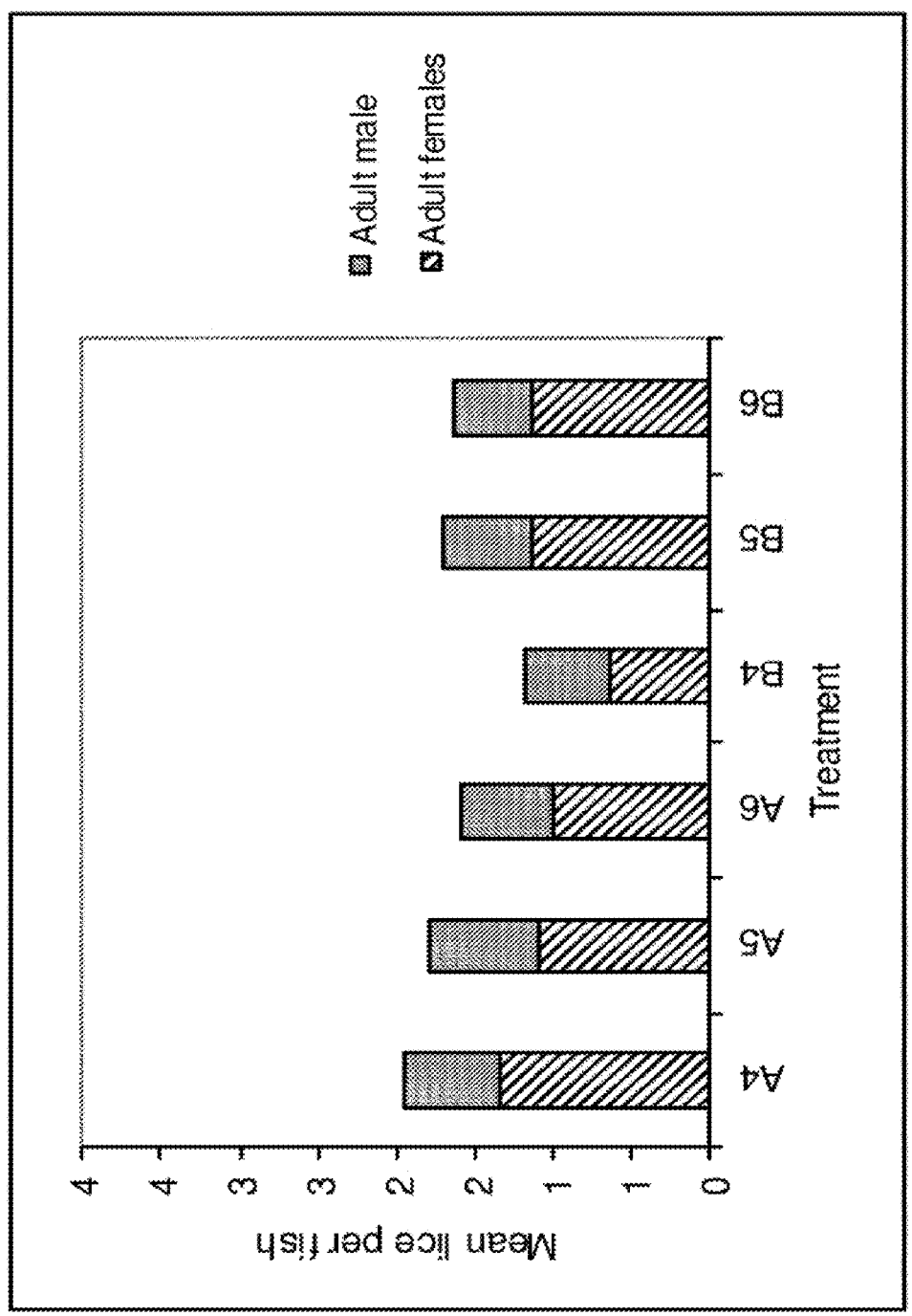
Figure 21:
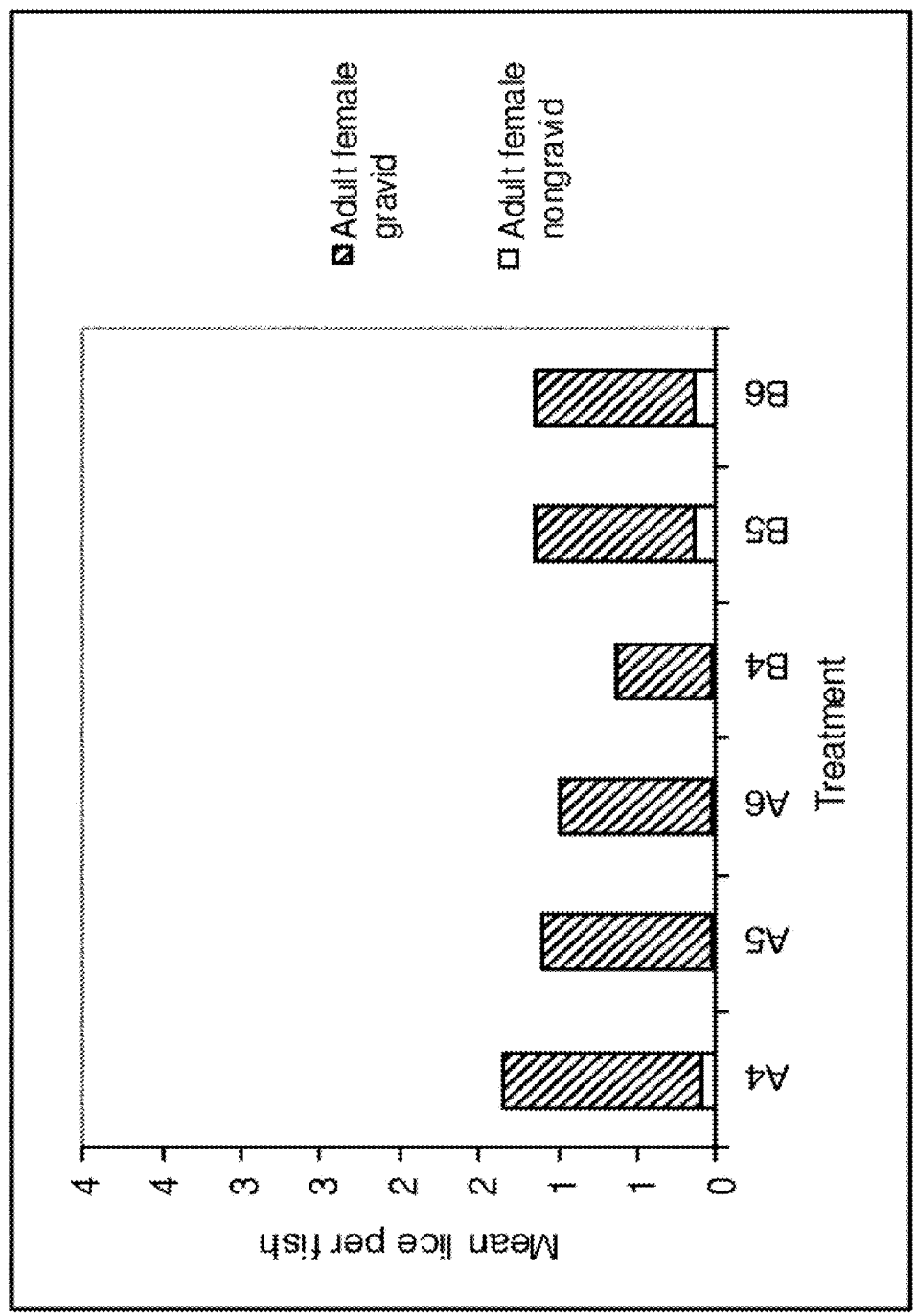

FIGS. 19, 20 and 21 represent the numbers of lice, male and female and their fecundity at various stages of development 4 weeks after treatment.

The lice challenge was made one week before counting, and 4 weeks after the active ingredient-comprising diet had ceased. The results indicate that the effectiveness of the systemic active ingredient materials had ceased.

Figure 22:
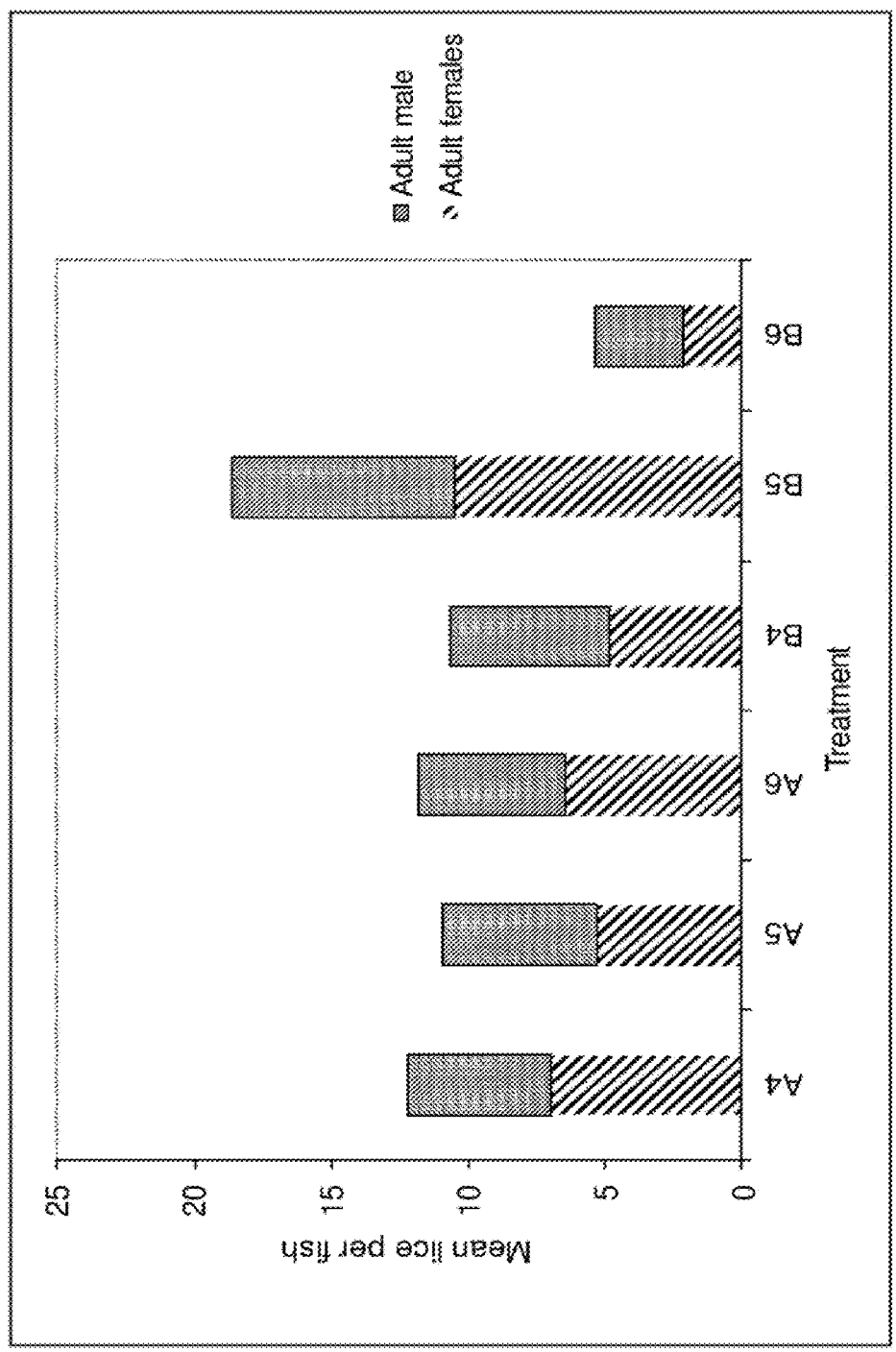

FIG. 22 represents the numbers of adult lice, male and female, 3 weeks after lice challenge, and 7 weeks after treatment. The results emphasise that the lice had no restriction to their development into adults between 4-7 weeks after treatment, confirming that an effective amount of the active ingredients was no longer present in the fish.

Figure 23:
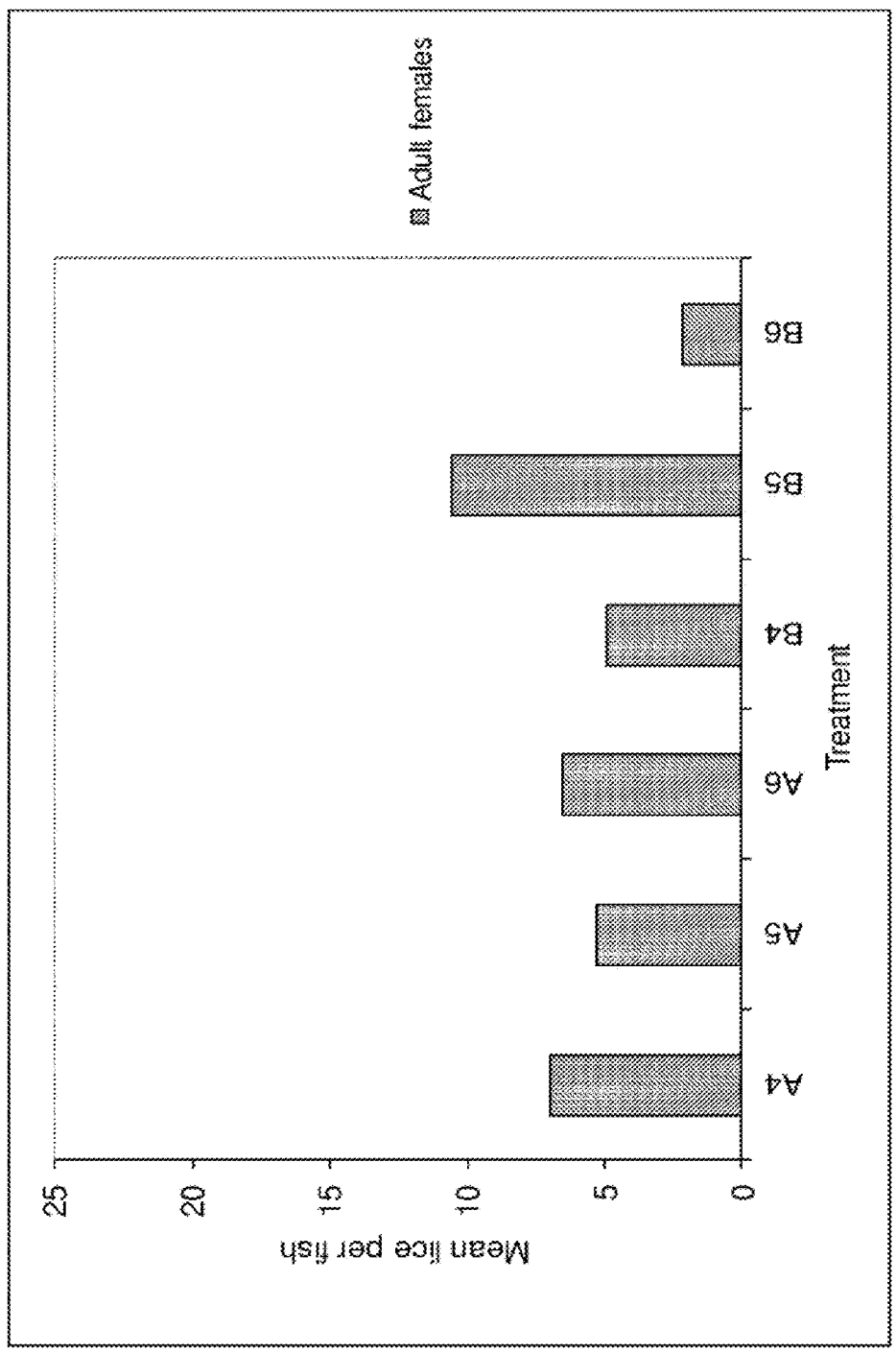
Figure 24:
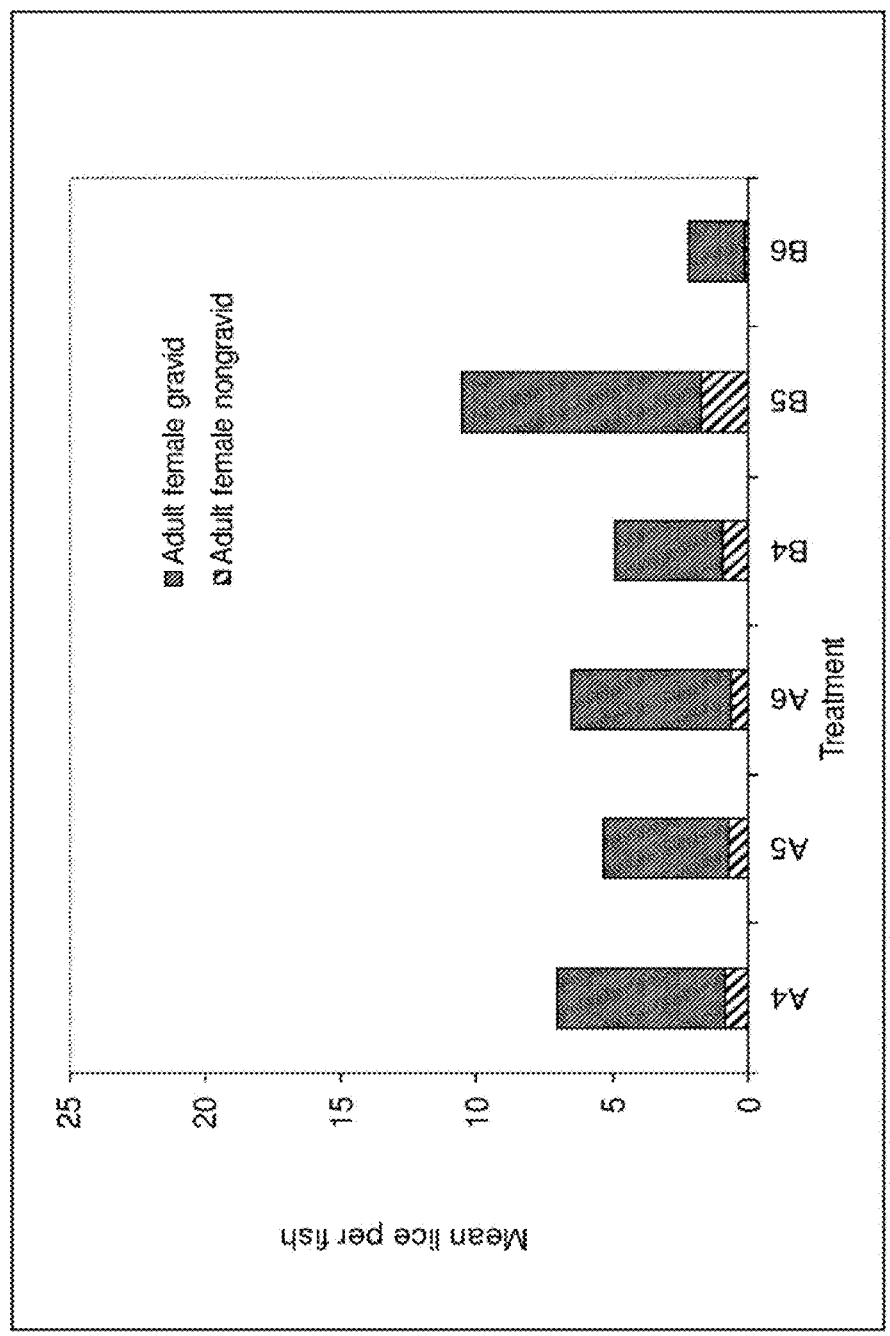

FIGS. 23 and 24 represent the numbers and fecundity of female lice 3 weeks after lice challenge and 7 weeks after treatment. With the exception of one of the test tanks, there was no difference either in numbers of adult females or in their fecundity.

Conclusions

The treatment with NeemAzal® comprising fish feed was very effective at reducing numbers of attached chalimi, by over 90%.

Treatment was effective at reducing numbers of pre-adults, to a lesser extent, with females being more affected than males (17% of pre-adult male reduction and 76% of pre-adult female reduction).

The treatment had a small effect on the numbers of adult lice, the females being slightly reduced and the number of males being similar in treated and untreated groups.

The treatment effectively eliminated egg production in gravid females. The treatment prevented egg production in developing lice that survived the treatment

Additional Data

Figure 25:
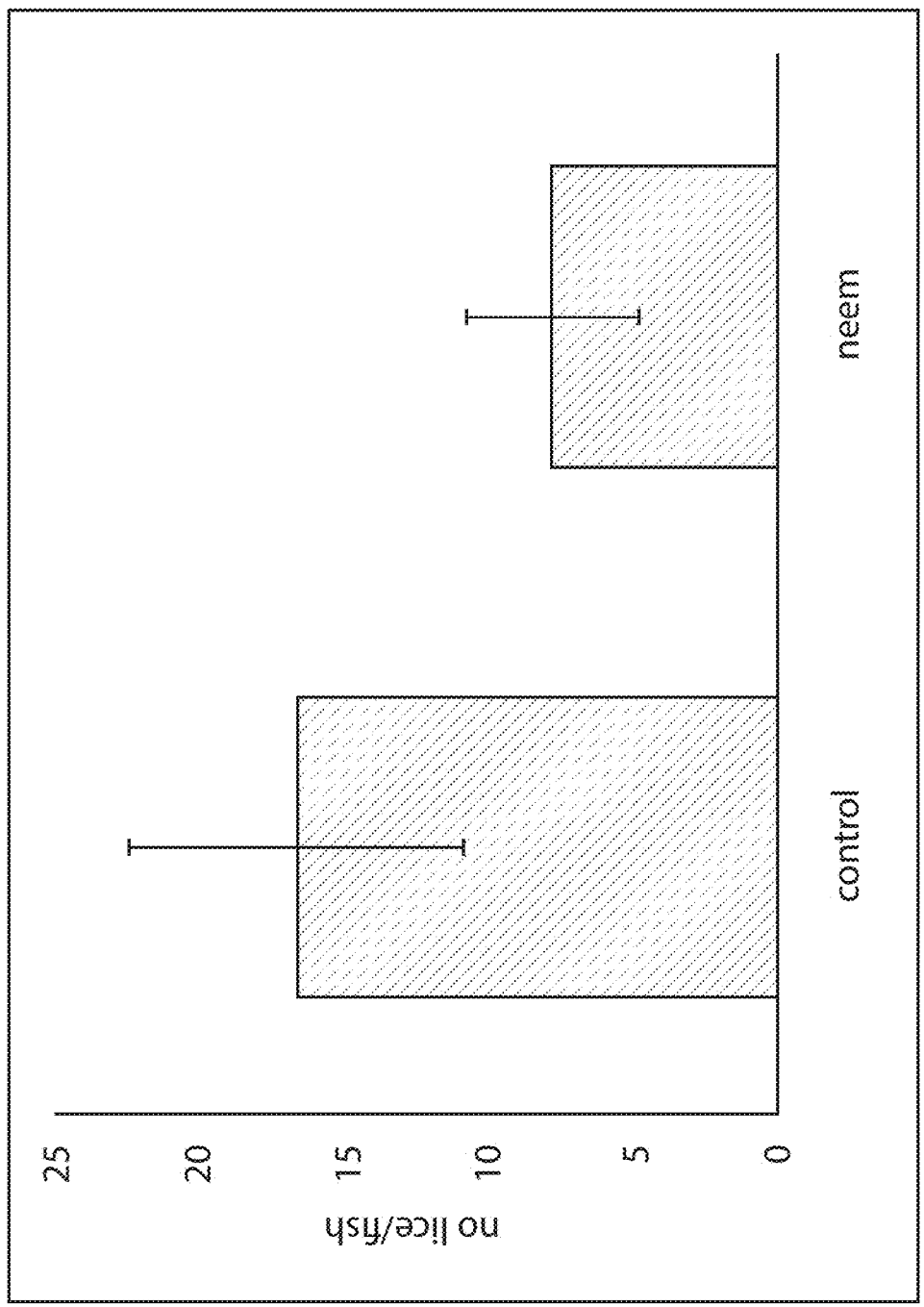
Figure 26:
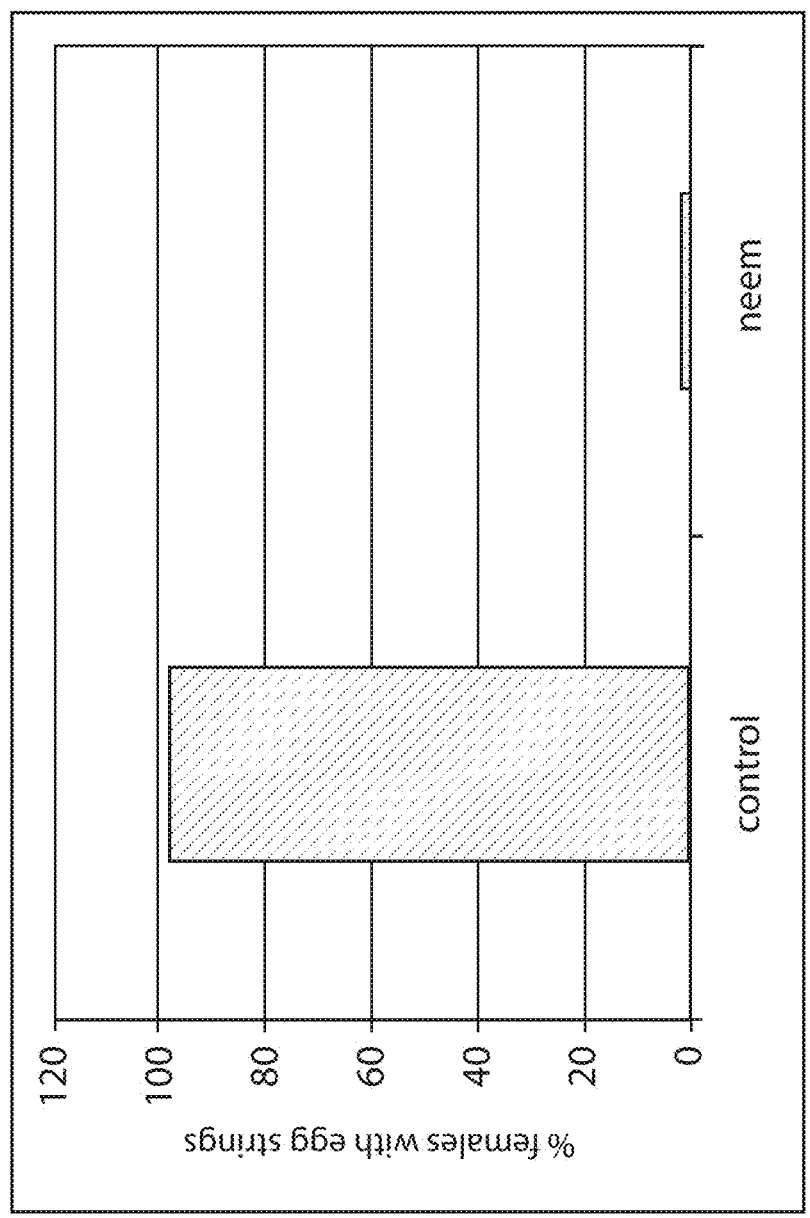

Two tanks of thirty-five Atlantic salmon were experimentally infected with sea lice which were then allowed to develop to the motile adult male and gravid adult female stages. Fish in one tank were treated by voluntary feeding using medicated feed containing the neem-based product (NeemAzal®) at a dose of 25 mg/kg biomass per day for 7 days, the other tank was left untreated. The medicated feed appeared to be consumed well and there were no mortalities or signs of adverse reaction in any of the test fish. Numbers of attached sea lice, counted 3 weeks post-treatment, were significantly lower in the tank treated with the neem-based product (7.8±3 lice per fish in the treated tank vs. 16.71±5.8 lice per fish in the control tank). The results are shown in FIG. 25. In addition, egg production in female lice infecting treated fish had been reduced substantially. Of a total of 117 adult female lice on the treated fish, only two had egg strings (1.7%). In the control tank, a total of 177 adult female lice were recorded of which 173 had egg strings (97.7%). The results are shown in FIG. 26.

Characteristics of Azadirachtin A

CIPAC No.: 627
CAS No.: 11141-17-6
Molecular Formula: C35 H44 O16
Molecular Mass: 720.7 g.mol-1
Solubility in water (20° C.): 2.9 g.L-1
Log Pow: 0.85-0.95
DT50 in fresh water: pH 4.0: 50 days
pH 7.0: 19 days
pH 8.0: 4 days
DT50 (daylight): 118 min
DT50 in field soil (20° C.): 4-5 days DT50 in sea water (16° C.): 8 days (Not GLP/GEP)
DT50 in fish-farm sediment (Skye): 3 weeks (Not GLP/GEP)

What is claimed is:

1. A method of controlling, preventing, and/or treating sea lice infections and/or infestations or copepod infections and/or infestations of fish, said method comprising:
administering to fish infected or infested with sea lice or copepods a fish feed comprising a neem extract rich in azadirachtin A, the neem extract comprising (% w/w):
(i) 34% w/w of Azadirachtin A;
(ii) about 5.5% w/w of Azadirachtin B;
(iii) about 2.1% w/w of Azadirachtin D;
(iv) 1.0% w/w or less of w/w Azadirachtin E;
(v) 1.0% w/w or less of Azadirachtin F;
(vi) 1.0% w/w or less of Azadirachtin G;
(vii) about 2.3% w/w of Azadirachtin H;
(viii) about 0.8% w/w of Azadirachtin I;
(ix) less than 2.0% w/w Azadirachtin K and other Azadirachtins; and
(x) about 2.0% w/w of Azadirachtinin; and
wherein the neem extract rich in azadirachtin A is present in the fish feed at a concentration of from about 0.1 grams to 100 grams azadirachtin A per kilogram of fish feed.

2. The method of claim 1, wherein the neem extract rich in azadirachtin A is obtained by a method comprising the steps of:
providing neem seeds;
crushing the neem seeds;
extracting azadirachtin from the crushed seeds with water;
adding a second extraction solution which comprises:
a non-aqueous solvent which is not miscible with water and has a higher solubility of azadirachtin than water; or
a surfactant having a turbidity temperature between 20° C. and 80° C.; and
recovering the concentrated azadirachtin from the second extraction solution.

3. The method of claim 1, wherein the neem extract rich in azadirachtin A does not comprise neem oil.

4. The method of claim 1, wherein the neem extract rich in azadirachtin A is administered to the fish at a concentration of from 1-60 mg azadirachtin A per kg body weight per day.

5. The method of claim 1, wherein the neem extract rich in azadirachtin A is administered to the fish for one to 10 days.

6. The method of claim 1, wherein the neem extract rich in azadirachtin A is present in the fish feed in an amount effective to remove up to at least 92% of sea lice in a chalimus to pre-adult life stage from the fish at seven days post administration as compared to fish not administered the fish feed comprising the neem extract rich in azadirachtin A.

7. The method of claim 1, wherein the neem extract rich in azadirachtin A is present in the fish feed in an amount effective to remove up to at least 76% of female sea lice proceeding from a pre-adult to adult stage from the fish at seven days post administration as compared to fish not administered the fish feed comprising the neem extract rich in azadirachtin A.

8. The method of claim 1, wherein the neem extract rich in azadirachtin A is present in the fish feed in an amount effective to remove up to at least 64% of adult male sea lice and up to at least 90% of adult female sea lice from the fish at three weeks post administration as compared to fish not administered the fish feed comprising the neem extract rich in azadirachtin A.

9. The method of claim 1, wherein the neem extract rich in azadirachtin A is present in the fish feed in an amount effective to reduce egg string production by adult female sea lice by up to at least 93% from the fish at seven days post administration as compared to fish not administered the fish feed comprising the neem extract rich in azadirachtin A.

10. The method of claim 1, wherein the neem extract rich in azadirachtin A present in the fish feed in an amount effective to remove up to at least 93% of gravid female sea lice from the fish at seven days post administration as compared to fish not administered the fish feed comprising the neem extract rich in azadirachtin A.

11. The method of claim 1, wherein the fish feed further comprises one or more components selected from the group consisting of: antibiotic agents, anti-bacterial agents, anti-fungal agents, anti-viral agents, anti-parasitic agents, anti-protozoal agents, or nutritional supplements.

12. The method of claim 1, wherein the fish feed is administered to species of fish belonging to one or more families selected from the group consisting of Cyprinidae, Cichlidae, Pangasiidae, Sciaenidae, Serranidae, Carangidae, Sparidae, Lateolabracidae, Moronidae, Mugilidae, Cypriniformes, Latidae, Eleotridae, Tilapiini, and Salmonidae.

13. The method of claim 1, wherein the parasite infection comprises an infection with or infestation with a copepod comprising one or more species of *Caligus* or *Lepeopththeirus*.

14. The method of claim 1, wherein the parasite infection comprises an infection with or infestation with a copepod comprising one or more of *Caligus clemensi, Caligus rogercreseyi*, or *Lepeopththeirus salmonis*.

15. The method of claim 1, wherein the fish feed comprising the neem extract rich in azadirachtin A is administered to the fish for seven days at a concentration of 10 mg azadirachtin A per kilogram body weight per day.

16. A method of controlling, preventing, and/or treating lice infections and/or infestations or copepod infections and/or infestations of fish, said method comprising administering to fish infected or infested with sea lice or copepods a fish feed comprising a neem extract rich in azadirachtin A, the neem extract comprising (% w/w):
(i) 34% w/w of Azadirachtin A;
(ii) about 5.5% w/w of Azadirachtin B;
(iii) about 2.1% w/w of Azadirachtin D;
(iv) 1.0% w/w or less of w/w Azadirachtin E;
(v) 1.0% w/w or less of Azadirachtin F;
(vi) 1.0% w/w or less of Azadirachtin G;
(vii) about 2.3% w/w of Azadirachtin H;
(viii) about 0.8% w/w of Azadirachtin I;
(ix) less than 2.0% w/w Azadirachtin K and other Azadirachtins; and
(x) about 2.0% w/w of Azadirachtinin; and
wherein the dose of azadirachtin A administered to the fish through the fish feed is from about 0.01 w/w % to 1.0 w/w % (azadirachtin A/fish feed).

17. The method of claim 16, further comprising examining the fish for sea lice number and sea lice life stage at seven days or three weeks post administration of the fish feed and determining an anti-fecundity effect of the neem extract rich in azadirachtin A on the sea lice or copepods.

18. The method of claim 17, wherein the anti-fecundity effect comprises one or more of a reduction in total number of egg strings produced by adult females and a reduction in total number of gravid females.

19. The method of claim 16, further comprising examining the fish for sea lice number and sea lice life stage at seven days or three weeks post administration of the fish feed and determining an efficacy effect of the neem extract rich in azadirachtin A on the sea lice or copepods.

20. The method of claim 19, wherein the efficacy effect comprises one or more of a reduction in total number of chalimus to pre-adults, a reduction in total number of pre-adult females, and a reduction in total number of adult females, a reduction in total number of adult males.

\* \* \* \* \*

UNITED STATES PATENT AND TRADEMARK OFFICE
CERTIFICATE OF CORRECTION

PATENT NO. : 12,082,597 B2
APPLICATION NO. : 18/050641
DATED : September 10, 2024
INVENTOR(S) : Michael Paul Mason and Robin Henderson Strang Page 1 of 1

It is certified that error appears in the above-identified patent and that said Letters Patent is hereby corrected as shown below:

On the Title Page

Column 1, Line 2, item (30) delete "PCT/GB2014/040803" and insert -- PCT/GB2014/050803 --, therefor.

In the Specification

In Column 8, Line 10, Delete "anon-nutritional" and insert -- a non-nutritional --, therefor.

Signed and Sealed this
Twenty-fifth Day of March, 2025

Coke Morgan Stewart
*Acting Director of the United States Patent and Trademark Office*